United States Patent [19]
Karp et al.

[11] Patent Number: 6,121,202
[45] Date of Patent: Sep. 19, 2000

[54] THIENYLOXYPYRIDINES AND-PYRIMIDINES USEFUL AS HERBICIDAL AGENTS

[75] Inventors: Gary Mitchell Karp; Michael Edward Condon, both of Mercer, N.J.

[73] Assignee: American Cyanamid Company, Madison, N.J.

[21] Appl. No.: 09/185,026

[22] Filed: Nov. 3, 1998

Related U.S. Application Data

[60] Provisional application No. 60/064,815, Nov. 7, 1997.

[51] Int. Cl.$^7$ .................. A01N 43/54; C07D 407/12; C07D 409/12
[52] U.S. Cl. ............. 504/242; 504/243; 54/319; 546/280.4; 546/281.4; 546/283.4; 546/284.4; 546/284.7; 549/61; 549/62; 549/66
[58] Field of Search .................... 504/242, 243; 544/319

[56] References Cited

U.S. PATENT DOCUMENTS 4,931,570  6/1990  Meul .......................... 549/62

FOREIGN PATENT DOCUMENTS

| | | |
|---|---|---|
| 0 186 252 | 12/1985 | European Pat. Off. . |
| 0 572 093 A1 | 12/1993 | European Pat. Off. . |
| 0693490 A1 | 1/1996 | European Pat. Off. . |
| 0 723 960 A1 | 7/1996 | European Pat. Off. . |
| 03232884 | 10/1991 | Japan . |
| 03279382 | 12/1991 | Japan . |
| 06025222 | 7/1992 | Japan . |
| 07138255 | 11/1993 | Japan . |
| 94/22833 | 10/1994 | WIPO . |
| 98/04550 | 2/1998 | WIPO . |

*Primary Examiner*—Mukund Shah
*Assistant Examiner*—Venkataraman Balasubramanian
*Attorney, Agent, or Firm*—Charles F. Costello, Jr.

[57] ABSTRACT

The present invention provides a herbicidal compound of formula I, methods for the preparation thereof and intermediates useful therefor.

(I)

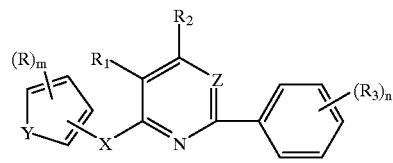

wherein X and Y are each independently O or S;
  Z is N or $CR_4$.

21 Claims, No Drawings

THIENYLOXYPYRIDINES AND-PYRIMIDINES USEFUL AS HERBICIDAL AGENTS

This application claims priority to U.S. Provisional Application No. 60/064815 filed Nov. 7, 1997.

BACKGROUND OF THE INVENTION

Mankind is dependent upon field crops for food, fiber, animal feed and the like. The ever-increasing world population dictates the necessity to produce more from each hectare and, at the same time, to preserve and protect the environment and natural resources that make such production possible. Successful crop production and environmental concerns lead to an ongoing need for new and effective methods to control pestiferous plants which provide early season weed competition and late season weed flushes causing significant loss in crop quality and yield.

Herbicidal 2,6-disubstituted pyridines and 2,4-disubstituted pyrimidines are described in EP 723,960. Said compounds contain a heteroaryloxy group in the 2 or 6 position wherein the heteroaryl moiety contains at least one nitrogen atom. Although many of these disclosed pyridine and pyrimidine compounds demonstrate efficacious control of a variety of weeds, said compounds are not completely satisfactory with regard to crop selectivity and consequently may have limited application in agricultural practice.

It has now been found that the 2-(thienyloxy)-pyridine and 6-(thienyloxy)pyrimidine compounds of the present invention are particularly useful as crop-selective herbicidal agents.

SUMMARY OF THE INVENTION

The present invention provides a thienyloxy compound of formula I

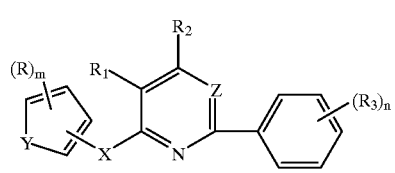

(I)

wherein X and Y are each independently O or S;

Z is N or $CR_4$;

m is 0 or an integer of 1, 2 or 3;

n is 0 or an integer of 1, 2, 3, 4 or 5;

R is halogen, $C_1$–$C_6$alkyl optionally substituted with one or more halogen, $C_1$–$C_4$alkoxy, $C_1$–$C_4$haloalkoxy, $C_1$–$C_4$alkoxycarbonyl, OH, CN, $NO_2$, $R_5SO_z$, $CY'R_7$, or phenyl groups, $C_2$–$C_6$alkenyl optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_5SO_z$, or phenyl groups, $C_3$–$C_6$alkynyl optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_5SO_z$, or phenyl groups, $C_1$–$C_6$alkoxy optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_5SO_z$, or phenyl groups, phenyl optionally substituted with one or more halogen, $C_1$–$C_4$alkyl, $C_1$–$C_4$haloalkyl, $C_1$–$C_4$alkoxy, $C_1$–$C_4$haloalkoxy, $R_5SO_z$, CN, $NO_2$, $CO_2R_6$ or $CY'R_7$ groups, $R_5SO_z$, $SF_5$, $NO_2$, CN, $CO_2R_6$, $CY'R_7$, $OR_8$, $OCOR_9$ or $NR_{10}R_{11}$;

$R_1$ and $R_2$ are each independently H, halogen, $C_1$–$C_6$alkyl optionally substituted with one or more halogen, $C_1$–$C_4$alkoxy, $C_1$–$C_4$alkylthio, $C_1$–$C_4$haloalkoxy, $C_1$–$C_4$alkoxycarbonyl, OH, CHO, CN, $NO_2$, $R_{11}SO_x$, or phenyl groups, $C_2$–$C_6$alkenyl optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_{11}SO_x$, or phenyl groups, $C_3$–$C_6$alkynyl optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_{11}SO_x$, or phenyl groups, $C_1$–$C_6$alkoxy optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_{11}SO_x$, or phenyl groups, $R_{11}SO_x$, $NR_{12}R_{13}$, CN, $CZ'R_{14}$ or formamidine;

$R_3$ is halogen, $C_1$–$C_6$alkyl optionally substituted with one or more halogen, $C_1$–$C_4$alkoxy, $C_1$–$C_4$haloalkoxy, $C_1$–$C_4$alkoxycarbonyl, OH, $CX'R_{15}$, CN, $NO_2$, $R_{16}SO_y$ or phenyl groups, $C_2$–$C_6$alkenyl optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_{16}SO_y$ or phenyl groups, $C_3$–$C_6$alkynyl optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_{16}SO_y$ or phenyl groups, $C_1$–$C_6$alkoxy optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_{16}SO_y$ or phenyl groups, $R_{16}SO_y$, $NR_{17}R_{18}$, $NO_2$, CN, $CX'R_{15}$, $CO_2R_{19}$ or $OCOR_{20}$;

X', Y' and Z' are each independently O, $NOR_{21}$ or $NNR_{22}R_{23}$;

$R_4$ is H, halogen, $C_1$–$C_6$alkyl or $C_1$–$C_6$haloalkyl;

$R_5$, $R_{11}$, and $R_{16}$ are each independently $C_1$–$C_4$alkyl or $C_1$–$C_4$haloalkyl;

$R_6$, $R_7$, $R_9$, $R_{14}$, $R_{15}$, $R_{19}$ and $R_{20}$ are each independently H or $C_1$–$C_4$alkyl optionally substituted with one or more halogen, phenyl or furyl groups;

$R_8$ is H, $C_1$–$C_6$alkyl optionally substituted with one or more halogen, $C_1$–$C_4$alkoxy, $C_1$–$C_4$haloalkoxy, $C_1$–$C_4$alkoxycarbonyl, OH, CN, or $NO_2$ groups, phenyl optionally substituted with one or more halogen, $C_1$–$C_4$alkoxy, $C_1$–$C_4$haloalkoxy, $C_1$–$C_4$alkoxycarbonyl, OH, CN or $NO_2$ groups;

$R_{10}$, $R_{11}$, $R_{12}$, $R_{13}$, $R_{17}$, $R_{18}$, $R_{22}$ and $R_{23}$ are each independently H, $C_1$–$C_4$alkyl or $C_1$–$C_4$alkoxy;

$R_{21}$ is H or $C_1$–$C_4$alkyl; and x, y and z are each independently 0 or an integer of 1 or 2.

The present invention also provides a compound of formula IIIA $$\text{(IIIA)}$$

wherein Q is CN, $R_{24}SO_z$, $C_1-C_6$alkyl optionally substituted with one or more halogen, $C_1-C_4$alkoxy, $C_1-C_4$haloalkoxy, $C_1-C_4$alkoxycarbonyl, phenyl optionally substituted with one or more halogen, $C_1-C_4$alkyl or $C_1-C_4$-haloalkyl groups, OH, CHO, CN, $NO_2$, or $R_5SO_z$ groups, $C_1-C_4$alkoxy optionally substituted with one or more halogen, OH, CHO, CN, $NO_2$ or $R_5SO_z$ groups, $R_5$ is $C_1-C_4$alkyl or $C_1-C_4$haloalkyl;

$R_{24}$ is $C_1-C_4$haloalkyl; and z is 0 or an integer of 1 or 2.

The present invention further provides a compound of formula IV $$\text{(IV)}$$

wherein X and Y are each independently O or S;

Z is N or $CR_4$;

m is 0 or an integer of 1, 2 or 3;

n is 0 or an integer of 1, 2, 3, 4 or 5;

R is halogen, $C_1-C_6$alkyl optionally substituted with one or more halogen, $C_1-C_4$alkoxy, $C_1-C_4$haloalkoxy, $C_1-C_4$alkoxycarbonyl, OH, CN, $NO_2$, $R_5SO_z$, $CY'R_7$, or phenyl groups, $C_2-C_6$alkenyl optionally substituted with one or more halogen, $C_1-C_4$alkoxy, $C_1-C_4$haloalkoxy, $C_1-C_4$alkoxycarbonyl, OH, CHO, CN, $NO_2$, $R_5SO_z$, or phenyl groups, $C_3-C_6$alkynyl optionally substituted with one or more halogen, $C_1-C_4$alkoxy, $C_1-C_4$haloalkoxy, $C_1-C_4$alkoxycarbonyl, OH, CHO, CN, $NO_2$, $R_5SO_z$, or phenyl groups, $C_1-C_6$alkoxy optionally substituted with one or more halogen, $C_1-C_4$alkoxy, $C_1-C_4$haloalkoxy, $C_1-C_4$alkoxycarbonyl, OH, CHO, CN, $NO_2$, $R_5SO_z$, or phenyl groups, phenyl optionally substituted with one or more halogen, $C_1-C_4$alkyl, $C_1-C_4$haloalkyl, $C_1-C_4$alkoxy, $C_1-C_4$haloalkoxy, $R_5SO_z$, CN, $NO_2$, $CO_2R_6$ or $CY'R_7$ groups, $R_5SO_z$, $SF_5$, $NO_2$, CN, $CO_2R_6$, $CY'R_7$, $OR_8$, $OCOR_9$ or $NR_{10}R_{11}$;

$R_1$ is H, halogen, $C_1-C_6$alkyl optionally substituted with one or more halogen, $C_1-C_4$alkoxy, $C_1-C_4$alkylthio, $C_1-C_4$haloalkoxy, $C_1-C_4$alkoxycarbonyl, OH, CHO, CN, $NO_2$, $R_{11}SO_x$, or phenyl groups, $C_2-C_6$alkenyl optionally substituted with one or more halogen, $C_1-C_4$alkoxy, $C_1-C_4$haloalkoxy, $C_1-C_4$alkoxycarbonyl, OH, CHO, CN, $NO_2$, $R_{11}SO_x$, or phenyl groups, $C_3-C_6$alkynyl optionally substituted with one or more halogen, $C_1-C_4$alkoxy, $C_1-C_4$haloalkoxy, $C_1-C_4$alkoxycarbonyl, OH, CHO, CN, $NO_2$, $R_{11}SO_x$, or phenyl groups, $C_1-C_6$alkoxy optionally substituted with one or more halogen, $C_1-C_4$alkoxy, $C_1-C_4$haloalkoxy, $C_1-C_4$alkoxycarbonyl, OH, CHO, CN, $NO_2$, $R_{11}SO_x$, or phenyl groups, $R_{11}SO_x$, $NR_{12}R_{13}$, CN, $CZ'R_{14}$ or formamidine;

$R_3$ is H, halogen, $C_1-C_6$alkyl optionally substituted with one or more, halogen, $C_1-C_4$alkoxy, $C_1-C_4$haloalkoxy, $C_1-C_4$alkoxycarbonyl, OH, $CX'R_{15}$, CN, $NO_2$, $R_{16}SO_y$ or phenyl groups, $C_2-C_6$alkenyl optionally substituted with one or more halogen, $C_1-C_4$alkoxy, $C_1-C_4$haloalkoxy, $C_1-C_4$alkoxycarbonyl, OH, CHO, CN, $NO_2$, $R_{16}SO_y$ or phenyl groups, $C_3-C_6$alkynyl optionally substituted with one or more halogen, $C_1-C_4$alkoxy, $C_1-C_4$haloalkoxy, $C_1-C_4$alkoxycarbonyl, OH, CHO, CN, $NO_2$, $R_{16}SO_y$ or phenyl groups, $C_1-C_6$alkoxy optionally substituted with one or more halogen, $C_1-C_4$alkoxy, $C_1-C_4$haloalkoxy, $C_1-C_4$alkoxycarbonyl, OH, CHO, CN, $NO_2$, $R_{16}SO_y$ or phenyl groups, $R_{16}SO_y$, $NR_{17}R_{18}$, $NO_2$, CN, $CX'R_{15}$, $CO_2R_{19}$ or $OCOR_{20}$;

$X'$, $Y'$ and $Z'$ are each independently O, $NOR_{21}$ or $NNR_{22}R_{23}$;

$R_4$ is H, halogen, $C_1-C_6$alkyl or $C_1-C_6$haloalkyl;

$R_5$, $R_{11}$, and $R_{16}$ are each independently $C_1-C_4$alkyl or $C_1-C_4$haloalkyl;

$R_6$, $R_7$, $R_9$, $R_{14}$, $R_{15}$, $R_{19}$ and $R_{20}$ are each independently H or $C_1-C_4$alkyl optionally substituted with one or more halogen, phenyl or furyl groups;

$R_8$ is H, $C_1-C_6$alkyl optionally substituted with one or more halogen, $C_1-C_4$alkoxy, $C_1-C_4$haloalkoxy, $C_1-C_4$alkoxycarbonyl, OH, CN, or $NO_2$ groups, phenyl optionally substituted with one or more halogen, $C_1-C_4$alkoxy, $C_1-C_4$haloalkoxy, $C_1-C_4$alkoxycarbonyl, OH, CN or $NO_2$ groups;

$R_{10}$, $R_{11}$, $R_{12}$, $R_{13}$, $R_{17}$, $R_{18}$, $R_{22}$ and $R_{23}$ are each independently H, $C_1-C_4$alkyl or $C_1-C_4$alkoxy;

$R_{21}$ is H or $C_1-C_4$alkyl; and x, y and z are each independently 0 or an integer of 1 or 2.

Further provided are compositions and methods for the control of monocotyledenous and dicotyledenous plant species and processes to prepare herbicidal compounds of formula I employing the intermediate compounds of formula IIIA and formula IV.

DETAILED DESCRIPTION OF THE INVENTION

Improved crop production methods and new, effective herbicidal agents are continually being sought by agriculturalists around the world. Surprisingly, the formula I thienyloxy compounds, of the invention demonstrate excellent control of a wide variety of monocotyledenous and dicotyledenous weeds. Advantageously, the formula I compounds of the invention also demonstrate crop selectivity, particularly cereal crop selectivity, and especially corn selectivity.

In the specification and claims, halogen designates F, Cl, Br and I and haloalkyl designates an alkyl group $C_nH_{2n+1}$ having n to (2n+1) halogens which may be the same or different.

Preferred compounds of formula I are those compounds wherein X is O; Y is S; Z is N or $CR_4$ and $R_4$ is H.

A more preferred group of compounds of formula I are those compounds having formula IA

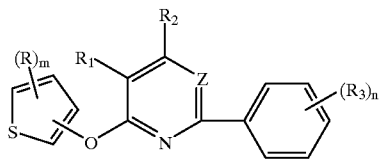

(IA)

wherein Z, R, $R_1$, $R_2$, $R_3$, m and n are as described for formula I.

Preferred compounds of formula IA are those compounds wherein n is 0 or an integer of 1, 2 or 3;

R is halogen, $R_5SO_2$, $CO_2R_6$, $COR_7$, CN, CHO, $NO_2$, $C_1$–$C_6$alkyl or $C_1$–$C_6$haloalkyl;

$R_1$ and $R_2$ are each independently H, halogen, $C_1$–$C_6$alkyl optionally substituted with one or more halogen, $C_1$–$C_4$alkoxy, $C_1$–$C_4$haloalkoxy or $C_1$–$C_4$alkylthio groups; $C_1$–$C_6$alkoxy, $R_{10}SO_x$ or CN;

$R_3$ is halogen, $C_1$–$C_6$alkyl, $C_1$–$C_6$haloalkyl or $R_{16}SO_y$;

$R_5$, $R_{10}$ and $R_{16}$ are each independently $C_1$–$C_4$alkyl or $C_1$–$C_6$haloalkyl;

$R_6$ and $R_7$ are each independently $C_1$–$C_6$alkyl or $C_1$–$C_6$haloalkyl;

y and z are each independently 0 or an integer of 1 or 2; and x is 0.

More preferred compounds of formula IA are those wherein m is 1; R is attached to the 5 position of the thienyloxy group; n is 1; and $R_3$ is attached to the 4 position of the phenyl group.

Another group of preferred compounds having the structure of formula IA are those compounds wherein R is $C_1$–$C_4$haloalkyl, $C_1$–$C_4$haloalkylcarbonyl, $C_1$–$C_4$alkylsulfonyl or $C_1$–$C_4$haloalkylsulfonyl, preferably $CF_3$, $COCF_3$, $CF_3SO_2$, $CH_3SO_2$, $CF_2Cl$ or $CHF_2$; $R_1$ and $R_2$ are each Independently H, halogen, $C_1$–$C_4$alkoxy or $C_1$–$C_4$alkyl optionally substituted with one or more $C_1$–$C_4$alkoxy groups; and $R_3$ is $CF_3$.

Examples of specific compounds of the invention include, but are not limited to: 4-Methyl-2-(α,α,α-trifluoro-p-tolyl)-6-{[5-(trifluoromethyl)-3-thienyl]oxy}-pyrimidine;

4-Methoxy-2-(α,α,α-trifluoro-p-tolyl)-6-{[5-(trifluoromethyl-3-thienyl]oxy}pyrimidine;

5-Ethyl-2-(α,α,α-trifluoro-p-tolyl)-6-{[5-(trifluoromethyl-3-thienyl]oxy}pyrimidine;

4-Methyl-6-(α,α,α-trifluoro-p-tolyl)-2-{[5-(trifluoromethyl)-3-thienyl]oxy}pyrimidine;

5-Methyl-2-(α,α,α-trifluoro-p-tolyl)-6-{[5-(trifluoromethyl-3-thienyl]oxy}pyrimidine;

5-Ethyl-2-(α,α,α-trifluoro-p-tolyl)-6-{[5-(trifluoromethylsulfonyl)3-thienyl]oxy}pyrimidine;

4-Ethyl-2-(α,α,α-trifluoro-p-tolyl)-6-{[5-(trifluoromethyl-3-thienyl]oxy}pyrimidine;

2-(α,α,α-Trifluoro-p-tolyl)-6-{[5-(trifluoromethyl-3-thienyl oxy}pyrimidine;

4-n-Propyl-2-(α,α,α-trifluoro-p-tolyl)-6-{[5-(trifluoromethyl-3-thienyl]oxy}pyrimidine;

4-Chloro-5-ethyl-2-(α,α,α-trifluoro-p-tolyl)-6-{[5-(trifluoromethyl-3-thienyl]oxy}pyrimidine;

4-Chloro-2-(α,α,α-trifluoro-p-tolyl)-6-{[5-(trifluoromethyl-3-thienyl]oxy}pyrimidine;

4-(Methoxymethyl)-2-((α,α,α-trifluoro-p-tolyl)-6-{[5-(trifluoromethyl-3-thienyl]oxy}pyrimidine;

4-Methyl-2-(α,α,α-trifluoro-p-tolyl)-6-{[5-(hydroxymethyl)-3-thienyl]oxy}pyrimidine;

4-(Difluoromethyl)-2-(α,α,α-trifluoro-p-tolyl)-6-{[5-(trifluoromethyl-3-thienyl]oxy}pyrimidine;

4-Methyl-6-(α,α,α-trifluoro-p-tolyl)-2-{[5-(trifluoromethyl-3-thienyl]oxy}pyridine;

4-Cyano-6-(α,α,α-trifluoro-p-tolyl)-2-{[5-(trifluoromethyl-3-thienyl]oxy}pyridine;

2-(α,α,α-Trifluoro-p-tolyl)-6-{[5-(trifluoromethyl-3-thienyl]oxy}pyridine;

3-Methyl-6-(α,α,α-trifluoro-p-tolyl)-2-{[5-(trifluoromethyl-3-thienyl]oxy}pyridine;

3-Methyl-6-(α,α,α-trifluoro-p-tolyl)-2-[(5-formyl-3-thienyl)oxy]pyridine;

4-Cyano-6-(α,α,α-trifluoro-p-tolyl)-2-{[5-(methylsulfonyl)-3-thienyl]oxy}pyridine;

2-(α,α,α-Trifluoro-p-tolyl)-6{[-5-(trifluoromethylsulfonyl)-3-thienyl]oxy}pyridine;

5-Ethyl-2-(α,α,α-trifluoro-p-tolyl)-6-{[5-(trifluorosulfonnyl)-3-thienyl]oxy}pyrimidine;

5-Methyl-2-(α,α,α-trifluoro-p-tolyl)-6-{[5-(methylsulfonyl)-3-thienyl]oxy}pyrimidine;

4-Methoxy-2-(α,α,α-trifluoro-p-tolyl)-6-[(5-formyl-3-thienyl)oxy]pyrimidine;

4-Ethyl-2-(α,α,α-trifluoro-p-tolyl)-6-{[5-(methylsulfonyl)-3-thienyl]oxy}pyrimidine;

4-Methyl-2-(α,α,α-trifluoro-p-tolyl)-6-{[5-(trifluoromethylsulfonyl)-3-thienyl]oxy}pyrimidine;

4-Cyano-2-(α,α,α-trifluoro-p-tolyl)-6-{[5-(methylsulfonyl)-3-thienyl]oxy}pyrimidine; and 5-Methoxymethyl-2-(α,α,α-trifluoro-p-tolyl)-6-{[5-(trifluoromethylsulfonyl)-3-thienyl]oxy}pyrimidine.

The compounds of the invention are oils, gums or, predominantly, crystalline solid materials. They may be prepared by reacting a compound of formula II

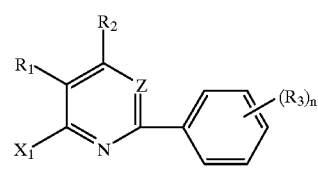

(II)

wherein $X_1$ is F, Cl or Br and Z, $R_1$, $R_2$, $R_3$ and n are as described for formula I with at least one molar equivalent of a compound of formula III

wherein X, Y, R and m are as described for formula I, in the presence of a base and optionally a solvent. The reaction is shown in flow diagram I.

Alternatively, compounds of formula I may be prepared by reacting a compound of formula II wherein $R_2$ is F, Cl or Br with at least 2 molar equivalents of a compound of formula III in the presence of a base and optionally a solvent to form a dithienyl(or furyl)oxy or -thioxy intermediate compound of formula IV wherein X, Y, Z, R, $R_1$, $R_3$, m and n are as described for formula I. Using conventional methods, the 4-thienyloxy group of the intermediate formula IV compound may be displaced by an alkanol or alkylthiol to give compounds of formula I wherein $R_2$ is alkoxy or alkylthio, or hydrolytically cleaved to give compounds of formula I wherein $R_2$ is hydrogen. The reaction scheme is shown in flow diagram II, wherein the alkanol or alkylthiol is an alkanol and the alkanol is methanol.

FLOW DIAGRAM II

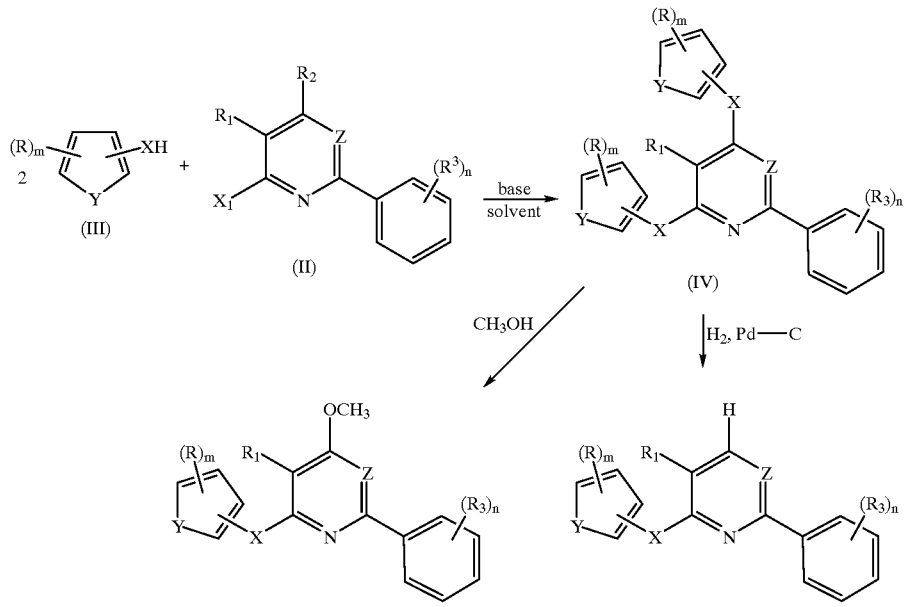

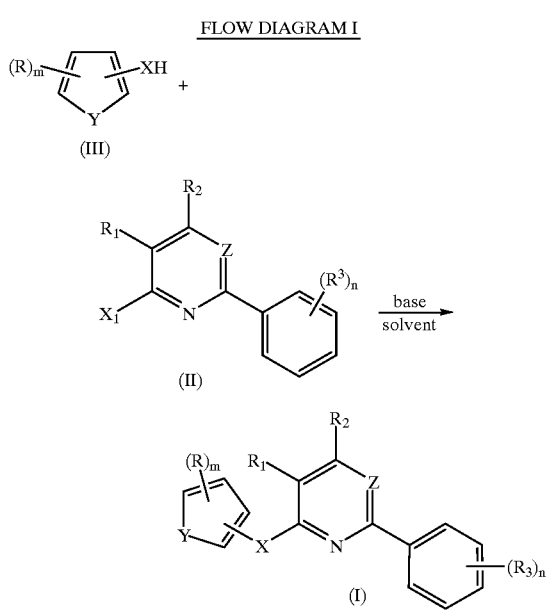

FLOW DIAGRAM I

Preferred formula IV compounds of the invention are those compounds wherein X is O; Y is S; Z is N or $CR_4$; and $R_4$ is hydrogen.

More preferred compounds of formula IV are those compounds having the structure of formula IVA

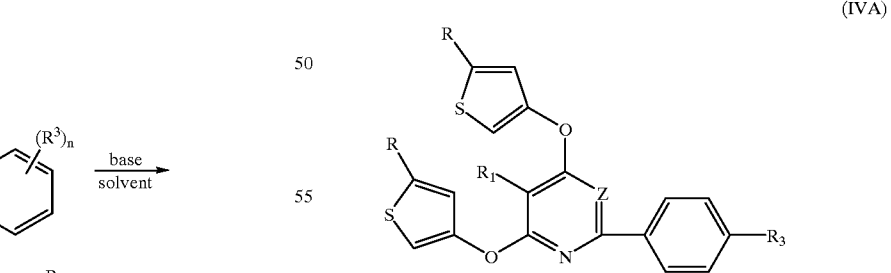

wherein Z, R, $R_1$ and $R_3$ are as described for formula I.

Particularly preferred are those compounds wherein R is $CF_3$ or $CH_3SO_2$; $R_1$ is hydrogen; $R_3$ is $CF_3$; Z is N or $CR_4$; and $R_4$ is hydrogen.

Compounds of formula III wherein X is O may be prepared according to conventional procedures such as the conjugative addition of the appropriately substituted butenoate of formula V with a glycolate or thioglycolate of formula VI in the presence of a base to form a thienyl-(or furyl)-2-carboxylate compound of formula VII. The formula VII compound may then be hydrolyzed to the corresponding carboxylic acid of formula VIII, which may then be decarboxylated to form the desired formula III compound wherein the hydroxyl group is attached in the 3 position. The reaction sequence is shown in flow diagram III.

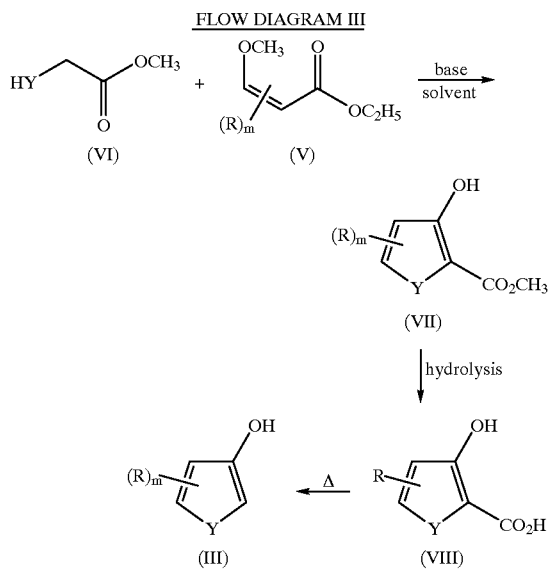

The present invention provides a compound of formula IIIA

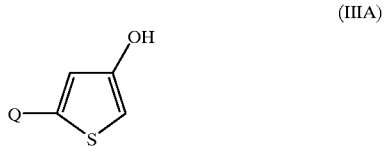

wherein Q is CN, $R_{24}SO_z$, $C_1-C_6$ alkyl optionally substituted with one or more halogen, $C_1-C_4$ alkoxy, $C_1-C_4$ haloalkoxy, $C_1-C_4$ alkoxycarbonyl, phenyl optionally substituted with one or more halogen, $C_1-C_4$ alkyl or $C_1-C_4$ haloalkyl groups, OH, CHO, CN, $NO_2$, or $R_5SO_z$ groups, $C_1-C_4$ alkoxy optionally substituted with one or more halogen, OH, CHO, CN, $NO_2$ or $R_5SO_z$ groups, $R_5$ is $C_1-C_4$ alkyl or $C_1-C_4$ haloalkyl;

$R_{24}$ is $C_1-C_4$ haloalkyl; and z is 0 or an integer of 1 or 2.

Preferred compounds of formula IIIA are those compounds wherein Q is $C_1-C_4$ haloalkyl or $C_1-C_4$ haloalkylsulfonyl and more preferably wherein Q is $CF_3$ or $CF_3SO_2$.

Compounds of formula IIIA are particularly useful for preparing many of the herbicidal compounds of formula IA when employed in the processes illustrated hereinabove in flow diagrams I and II.

The present invention also provides a method for the control of monocotyledenous and dicotyledenous annual, perennial and aquatic plant species which comprises applying to the foliage or to the soil or water containing the seeds or other propagating organs of said plants a herbicidally effective amount of a compound having the structure of formula I. Preferably the formula I compound is applied to said foliage, soil or water, more preferably to the soil or water, in the presence of a crop, particularly a cereal crop such as corn, rice, barley, wheat, oat; rye, and the like, especially corn.

In accordance with the method of the invention the formula I compounds may be applied alone or in combination with one or more conventional herbicides such as amethydione, bilanafos, metabenzthiazuron, metamitron, metribuzin, 2,4-D, 2,4-DB, 2,4-DP, alachlor, alloxydim, asulam, atrazine, bensulfuron, bentazon, bifenox, bromoxynil, butachlor, carfentratone, chloridazon, chlorimuron, chlorpropham, chlorsulfuron, chlortoluron, cinmethylin, clopyralid, cyanazine, cycloate, cyclosulfamuron, cycloxydim, dichlobenil, diclofop, dimethenamid, EPTC, ethiozin, fenoxaprop, flamprop, fluazifop, fluometuron, fluridone, fluroxypyr, fomesafen, glufosinate, glyphosate, haloxyfop, hexazinone, imazamethabenz, imazapic, imazamox, imazapyr, imazaquin, imazethapyr, ioxynil, isoproturon, isoxaflutole, lactofen, MCPA, MCPP, mefenacet, metazachlor, metolachlor, metsulfuron, molinate, norflurazon, oryzalin, oxyfluorfen, pendimethalin, picloram, pretilachlor, propachlor, pyridate, quizalofop, sethoxydim, simetryn, terbutryn, thiobencarb, triallate, trifluralin, diflufenican, propanil, triclopyr, dicamba, desmedipham, acetochlor, fluoroglycofen, halosafen, tralkoxydim, amidosulfuron, cinosulfuron, nicosulfuron, pyrazosulfuron, sulfentrazone, thiameturon, thifensulfuron, triasulfuron, tribenuron, esprocarb, prosulfocarb, terbutylazin, benfuresate, clomazone, dimethazone, dithiopyr, isoxaben, quinchlorac, quinmerac, sulfosate, or the like.

In actual practice, the effective amount of the formula I compound will vary according to the prevailing conditions such as time of application, mode of application, nature of the weed species, weed pressure, weather conditions, soil type, crop species, topography, and the like. In general rates of about 0.001 to 10 kg/ha, preferably about 0.01 to 1.0 kg/ha are suitable for effective weed control. It is of course obvious that greater rates of application can also be used to effectively control weeds, however rates of application of herbicides above the necessary level to control the undesirable weeds should be avoided since application of excessive amounts of herbicide is costly and serves no useful function in the environment.

In actual agricultural practice, compounds may be applied in the form of a spray, dust, granule, or the like. Advantageously, the present invention provides a herbicidal composition comprising an inert solid or liquid carrier and a herbicidally effective amount of a compound of formula I. In accordance with the composition of the invention, a carrier may be any material with which the formula I compound is formulated to facilitate field application or to facilitate storage, transport or handling.

Liquid carriers suitable for use in the composition of the invention include water; alcohols, such as isopropanol, glycols and the like; ketones, such as acetone, methyl ethyl ketone, methyl isobutyl ketone, cyclohexanone and the like; ethers; aromatic or araliphatic hydrocarbons, such as benzene, toluene, xylene and the like; petroleum fractions, such as kerosene, light mineral oils and the like; chlorinated hydrocarbons, such as carbon tetrachloride, perchloroethylene, trichloroethane and the like. Mixtures of different liquids are also often suitable.

Agricultural compositions may often be formulated and transported in a concentrated form and subsequently diluted by the user before application. The presence of small amounts of a surface-active agent facilitates this process of dilution. Thus, preferably a composition according to the invention may also comprisesa surface-active agent.

A surface-active agent may be an emulsifying agent, a dispersing agent or a wetting agent; it may be non-ionic or ionic. Examples of surface-active agents suitable for use in the composition of the invention include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or P-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkaryl sulphonates such as dodecylbenzene sulphonate; and polymers of ethylene oxide and copolymers of ethylene oxide and propylene oxide.

In accordance with the invention, herbicidal compositions may take the form of wettable powders, dusts, granules, solutions, emulsifiable concentrates, concentrated emulsions, suspension concentrates, aerosols and the like. Wettable powders usually contain about 25, 50 or 75% w of a compound of formula I and may comprise, in addition to solid inert carrier, about 3–10% w of a dispersing agent and, where necessary, about 0–10% w of a stabiliser(s) and/or other additives such as penetrants, stickers, and the like. Dusts are usually formulated as a dust concentrate having a similar composition to that of a wettable powder but without a dispersant, and may be diluted in the field with a further solid carrier to give a composition generally containing about 0.5–10% w of active ingredient. Granules having a particle size between 10 and 100 BS mesh (1.676–0.152 mm), may be prepared by agglomeration or impregnation techniques. Generally, granules may contain about 0.5–75% w of a formula I compound and 0–10% w of additives such as stabilisers, surfactants, slow release modifiers and binding agents. Dry flowable powders consist of relatively small granules having a relatively higher concentration of the formula I compound.

Emulsifiable concentrates generally comprise, in addition to a solvent and, when necessary, a co-solvent, about 10–50% w/v of a formula I compound, about 2–20% w/v emulsifiers and about 0–20% w/v of other additives such as stabilisers, penetrants and corrosion inhibitors. Suspension concentrates are usually compounded so as to obtain a stable, non-sedimenting flowable product and may comprise about 10–75% w of a formula I compound about 0.5–15% w of dispersing agents, about 0.1–10% w of suspending agents such as protective colloids and thixotropic agents, 0–10% w of other additives such as defoamers, corrosion inhibitors, stabilisers, penetrants and stickers, and water or an organic liquid in which the formula I compound is substantially insoluble; certain organic solids or inorganic salts may be dissolved in the formulation to assist in preventing sedimentation or as antifreeze agents.

Aqueous dispersions and emulsions, such as compositions obtained by diluting a wettable powder or a concentrate according to the invention with water, also lie within the scope of the invention. Said emulsions may be of the water-in-oil or of the oil-in-water type, and may have a thick mayonnaise-like consistency.

Examples of a herbicidal composition according to the invention include a composition which comprises about 100 g of a compound of formula I, about 30 g of a dispersing agent, about 3 g of an antifoaming agent, about 2 g of structure agent, about 50 g of an anti-freezing agent, about 0.5 g of a biocidal agent and water ad 1000 ml. Prior to use, the composition may be diluted with water to give the desired concentration of herbicide.

For a more clear understanding of the invention, specific examples are set forth below. These examples are merely illustrations and are not to be understood as limiting the scope and underlying principles of the invention in any way. Various modifications of the invention in addition to those shown and described herein will become apparent to those skilled in the art from the following examples and foregoing description. Such modifications are also intended to fall within the scope of the appended claims.

In the examples, the terms NMR and IR designate nuclear magnetic resonance and infrared spectroscopy, respectively. The terms GC, TLC and HPLC designate gas chromatography, thin layer chromatography and high performance liquid chromatography, respectively. Unless otherwise noted, all parts are by weight

EXAMPLE 1

Preparation of p-(Trifluoromethyl)benzamidine Hydrochloride

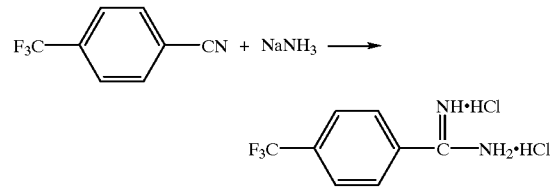

A stirred solution of p-(trifluoromethyl)-benzonitrile (100 g, 0.585 mol)in toluene is treated with $NaNH_2$ (38 g, 0.878 mol. 90% pure) and dibenzo-18-crown-6 (1.5 g), heated at reflux temperatures for 4 hours, cooled to 10° C. and treated slowly with 175 ml of concentrated HCl over a 30 minute period. The resultant reaction mixture is filtered and the filtercake is washed with toluene and dried to give a powdery yellowish solid. The solid is dissolved in ethanol and filtered. The filtrate is concentrated in vacuo to give a yellow solid residue. The residue is slurried in ethyl acetate and filtered. The filtercake is washed with ether and dried to give the title product as a yellow solid, 132.3 g (quantitative yield), identified by $_1HNMR$, $^{13}CNMR$ and $_{19}FNMR$ analyses.

EXAMPLE 2

Preparation of 6-Hydroxy-5-methyl-2-α,α,α(-trifluoro-p-tolyl)pyrimidine

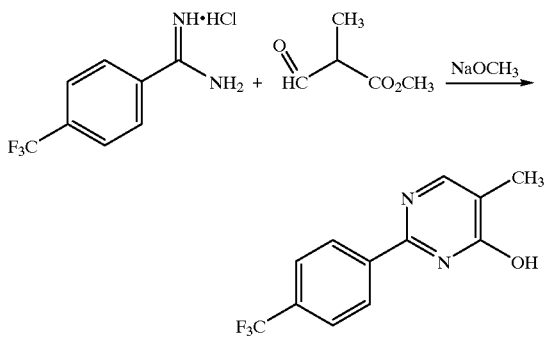

A mixture of p-(trifluoromethyl)benzamidine hydrochloride (31.7 g, 0.141 mol) and a 25% $NaOCH_3$ solution in methanol (60.9 g, 0.282 mol $NaOCH_3$) is stirred for 10 minutes, treated with methyl 2-formylpropionate (14.9 g, 0.128 mol) and stirred at ambient temperatures until reaction is complete by HPLC. The resultant reaction mixture is concentrated in vacuo to give a solid residue. The residue is treated with 1N NaOH, acidified with 10% HCl to pH 4 and filtered. The filtercake is washed with water and dried in vacuo to give the title product as a white solid, 30.35 g (85% yield), mp 273–275° C., identified by $^1$HNMR, $^{13}$CNMR and $^{19}$FNMR.

EXAMPLE 3

Preparation of Substituted 6-hydroxy-2-(α,α,α-trifluoro-p-tolyl)pyrimidine

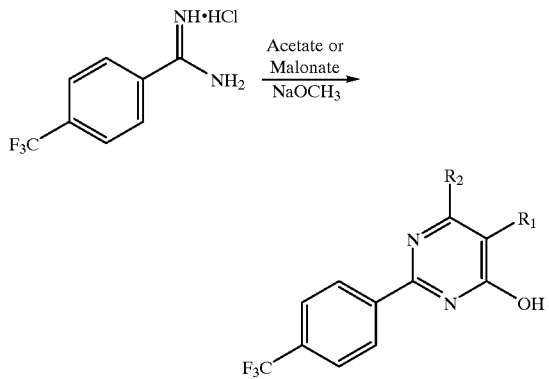

Using essentially the same procedure described in Example 2 and substituting the appropriate acetate or malonate reagent, the following substituted 2-hydroxypyrimidines are obtained. All compounds shown on Table I are identified by $^1$HNMR, $^{13}$CNMR and $^{19}$FNMR analyses.

TABLE I

| Reagent | $R_2$ | $R_1$ | mp ° C. | % yield |
|---|---|---|---|---|
| methyl propionylacetate | $C_2H_5$ | H | 181 | 86 |
| ethyl butyrylacetate | n-$C_3H_7$ | H | 138–141 | 59 |
| ethyl acetoacetate | $CH_3$ | H | 209 | 93 |
| methyl 4-methoxyacetoacetate | $CH_2OCH_3$ | H | 180–182 | 82 |
| dimethyl ethylmalonate | OH | $C_2H_5$ | >270 | 64 |
| dimethyl malonate | OH | H | >275 | 56 |

EXAMPLE 4

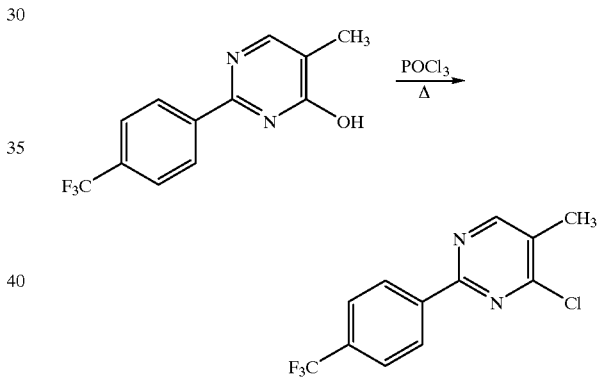

Preparation of 6-Chloro-5-methyl-2-(α,α,α-trifluoro-p-tolyl)pyrimidine

A mixture of 6-hydroxy-5-methyl-2-(α,α,α-trifluoro-p-tolyl)pyrimidine (5.00 g, 18.7 mmol) and 10 ml of $POCl_3$ is heated at reflux temperatures for 2 hours, allowed to cool to room temperature overnight and concentrated in vacuo to a thick paste residue. The residue is diluted with water and extracted with ethyl acetate.

The ethyl acetate extracts are combined, dried with brine and concentrated in vacuo to afford the title product as a tan solid, 2.72 g (51% yield) mp 110–112° C., identified by $^1$HNMR, $^{13}$CNMR and $^{19}$FNMR analyses.

EXAMPLE 5

Preparation of Substituted 6-chloro-2-(α,α,α-trifluoro-p-tolyl)pyrimidine

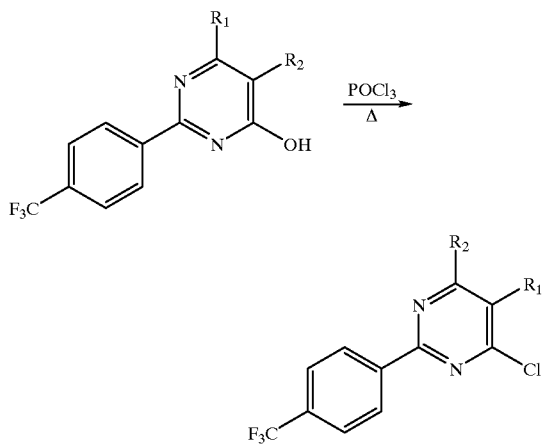

Using essentially the same procedure described in Example 4 and employing the appropriately substituted 6-hydroxypyrimidine, the following compounds are obtained. The compounds shown in Table II are identified by $^1$HNMR, $^{13}$CNMR and $^{19}$FNMR analyses.

TABLE II

| $R_2$ | $R_1$ | mp ° C. | % yield |
|---|---|---|---|
| $C_2H_5$ | H | 30–32 | 85 |
| n-$C_3H_7$ | H | oil | 80 |
| $CH_3$ | H | 62 | 91 |
| Cl | H | oil | 73 |
| Cl | $C_2H_5$ | 77–78 | 51 |
| $CH_2OCH_3$ | H | oil | 81 |

EXAMPLE 6

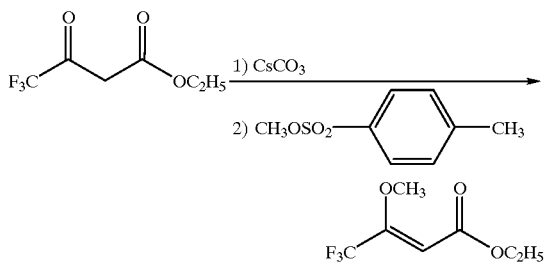

Preparation of Ethyl 3-Methoxy-4,4,4-trifluoro-2-buteneoate

A solution of ethyl trifluoromethylacetoacetate (75.0 g, 0.408 mol) in dimethylformamide is treated in one portion with $CsCO_3$ (132.8 g, 0.408 mol), allowed to exotherm (30–35° C.) and bubble, held at 70° C. with external heating for 15 minutes until bubbling ceased, treated slowly with a solution of methyl tosylate (83.4 g, 0.448 mol) in dimethylformamide over a 40 minute period at 70° C., held at 70° C. for 3 hours, cooled to room temperature and diluted with water. The resultant reaction mixture is extracted with ethyl acetate. The ethyl acetate extracts are combined, washed sequentially with water and brine, dried over $MgSO_4$ and concentrated in vacuo to give a yellow liquid residue. The residue is vacuum distilled, to give the title product as a clear liquid, 48.5 g (60% yield), bp 62–70°C./12 mm Hg, identified by GC, $^1$HNMR and $^{19}$FNMR analyses.

EXAMPLE 7

Preparation of Methyl 3-Hydroxy-5-trifluoromethyl-2-thiophenecarboxylate

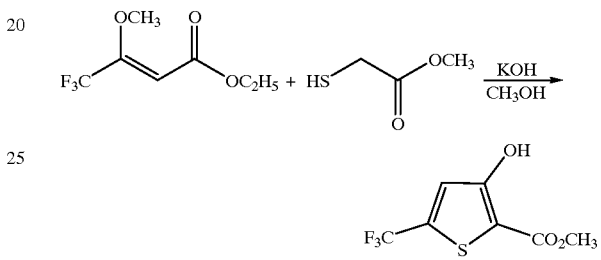

A solution of ethyl 3-methoxy-4,4,4-trifluoro-2-buteneoate (48.45 g, 0.245 mol) and methyl thioglycolate (25.95 g, 0.245 mole) in methanol is treated dropwise with 300 mL, 1M KOH/methanol over a 45 minute period at 35–42° C. (external cooling is used to control exotherm) and stirred at ambient temperatures until reaction is complete by GC analysis. The resultant reaction mixture is poured onto ice water, acidified with 6N $H_2SO_4$ to pH 2 and extracted with ethyl acetate. The ethyl acetate extracts are combined, washed sequentially with saturated $NaHCO_3$ and brine, dried over $MgSO_4$ and concentrated in vacuo to give a pale yellow liquid residue. The residue is vacuum distilled to give the title product as a clear liquid, 39.06 g (71% yield), bp 42–45° C./0.10 mm Hg, identified by $^1$HNMR, $^{13}$CNMR and $^{19}$FNMR analyses.

EXAMPLE 8

Preparation of 3-Hydroxy-5-trifluoromethyl-2-thioiphenecarboxylic Acid

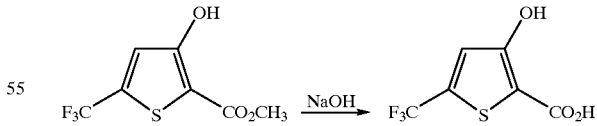

A stirred aqueous solution of NaOH (168 g, 4.21 mol) is treated with a solution of methyl 3-hydroxy-5-trifluoromethyl-2-thiophenecarboxylate (238 g, 1.05 mol) in methanol at ambient temperatures. When resultant exotherm has ceased, the reaction mixture is heated at reflux temperatures for 3 hours until hydrolysis is complete by TLC analysis, cooled to room temperature and concentrated in vacuo. The resultant concentrate is cooled to 5° C., acidified to pH 1 with concentrated HCl at temperatures below 10° C., stirred at 5° C. for 30 minutes and filtered. The filtercake is washed with water and dried to a constant weight to give the title product as a white solid, 145 g (65% yield), mp >100° C., decomposed, identified by $^1$HNMR analysis.

EXAMPLE 9

Preparation of 4-Hydroxy-2-(trifluoromethyl) thiophene

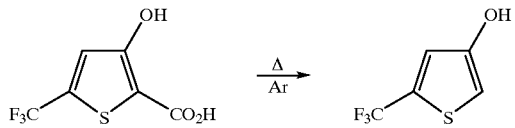

Neat 3-hydroxy-5-trifluoromethyl-2-thiophenecarboxylic acid (180 g, 0.849 mol) is slowly heated under argon to give rapid evolution of gas at 90° C. Heating at 90° C. is continued for an additional 3.5 hours. The resultant oil is vacuum distilled through a 6 inch Vigreaux column packed with ¼ inch glass cylinders to give the title product as a clear liquid, 118 g (82% yield), bp 70–74° C./4 mm Hg, identified by $^1$HNMR and $^{13}$CNMR analysis.

EXAMPLE 10

Preparation of Methyl 3-Benzyloxy-5-(methylsulfonyl)-2-thiophenecarboxylate

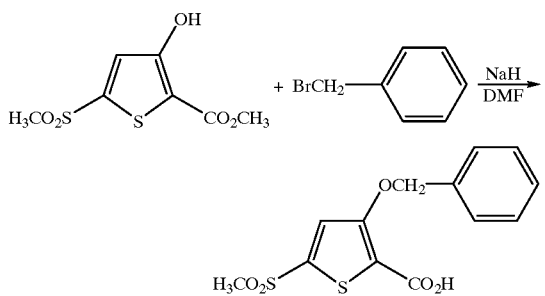

A mixture of NaH (3.18 g, 79.5 mmol) in dimethylformamide (DMF) is treated dropwise with a solution of methyl 3-hydroxy-5-(methylsulfonyl)-2-thiophenecarboxylate (15.0 g, 63.6 mmol) in DMF at 0° C., stirred for 10 minutes, treated with benzylbromide (8.30 ml, 70 mmol) at ice bath temperatures, allowed to warm to room temperature overnight and diluted with water. The resultant reaction mixture is filtered. The filtercake is washed with water, dried, stirred in a mixture of ethyl acetate/hexane (20 ml/130 ml), and filtered. The filtercake is washed with hexanes and dried in a Kugelrohr at 40° C. to give the title product as a white solid, 17.4 g (84% yield), mp 125–126° C. identified by $^1$HNMR, $^{13}$CNMR, IR and mass spectral analyses.

EXAMPLE 11

Preparation of 3-Benzyloxy-5-(methylsulfonyl)-2-thiophenecarboxylic Acid

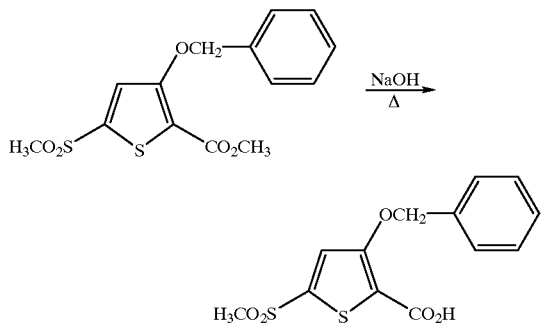

A mixture of methyl 3-benzyloxy-5-(methylsulfonyl)-2-thiophenecarboxylate (16.7 g, 51.2 mmol), 50 ml 2N NaOH and 50 ml of tetrahydrofuran is heated at reflux temperatures for 1 hour, cooled to room temperature and concentrated in vacuo to an aqueous residue. The residue is diluted with water, acidified to pH 1–2 with 6N HCl and filtered. The filtercake is washed with water and dried to give the title product as a white solid, 14.55 g (91% yield). A small sample was recrystallized from aqueous ethanol to give white needles, mp 188–189° C., identified by $^1$HNMR, $^{13}$CNMR, IR and mass spectral analyses.

EXAMPLE 12

Preparation of 4-Benzyloxy-2-(methylsulfonyl) thiophene

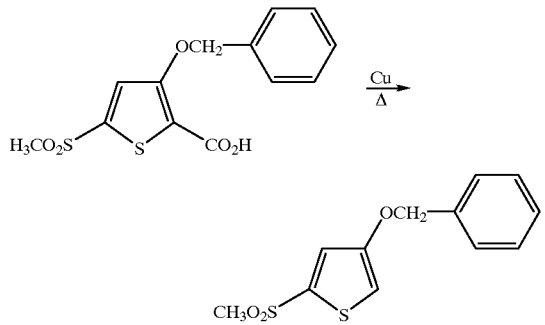

A solution of 3-benzyloxy-5-(methylsulfonyl)-2-thiopenecarboxylic acid (13.6 g, 43.6 mmol) in 50 ml quinoline is treated with Cu powder (4.15 g, 65.4 mmol) at room temperature, heated to 165° C. for 15 minutes, cooled to room temperature and filtered. (The filtercake is washed with water.) The combined filtrate is acidified to pH 1 with 6N HCl and filtered. This filtercake is washed with water and dried to afford the title product as a dark grey powder, 10.1 g (86% yield), mp 108–109° C., identified by $^1$HNMR, $^{13}$CNMR and mass spectral analyses.

EXAMPLE 13

Preparation of 4-Hydroxy-2-(methylsulfonyl)thiophene

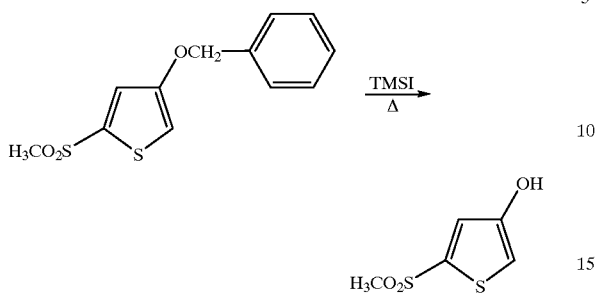

A solution of 3-benzyloxy-2-(methylsulfonyl)thiophene (8.82 g, 32.9 mmol) in acetonitrile is treated with trimethylsilyl iodide (TMSI) (9.36 ml, 65.8 mmole), heated at reflux temperatures for 1.25 hours, cooled to room temperature and concentrated in vacuo. The resultant residue is diluted with ethyl acetate, washed sequentially with water and brine, dried over $MgSO_4$ and concentrated in vacuo to give a brown residue. This residue is triturated under a mixture of ethyl acetate, hexanes and chloroform. The resultant slurry is filtered. The filtercake is dried in a Kugelrohr and chromatographed using flash column chromatography (silica gel, ethyl acetate) to afford a dark brown liquid. This liquid is treated with charcoal and filtered to give a yellow filtrate which is concentrated to afford the title product as a light brown solid, 4.0 g(68% yield) mp 109–111° C., identified by $^1$HNMR, $^{13}$CNMR, IR and mass spectral analyses.

EXAMPLE 14

Preparation of 4-Methyl-2-(α,α,α-trifluoro-p-tolyl)-6-{[5-(trifluoromethyl)-3-thienyl]oxy}pyrimidine

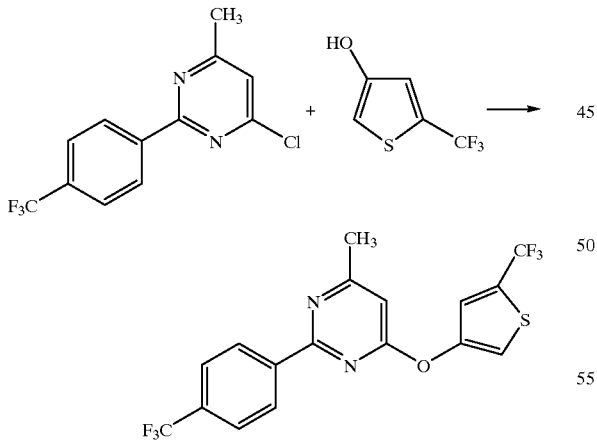

A mixture of 3-hydroxy-2-(trifluoromethyl)thiophene (0.50 g, 2.98 mmol) and 6-chloro-4-methyl-2-(α,α,α-trifluoro-p-tolyl)pyrimidine (0.31g, 2.98 mmol) in dimethylformamide is treated with $K_2CO_3$ (0.62 g, 4.47 mmol), heated at 100° C. for 17 hours, cooled to room temperature and diluted with water. The resultant reaction mixture is extracted with ether. The ether extracts are combined, washed sequentially with water and brine, dried over $MgSO_4$ and concentrated in vacuo to give a brown solid residue. The residue is chromatographed (silica gel, ethyl acetate/hexanes, 20/80) to give the title product as a light yellow solid, 0.88 g (73% yield), mp 83.5–85° C., identified by $^1$HNMR, $^{13}$CNMR, $^{19}$FNMR, mass spectral and elemental analyses.

EXAMPLE 15–27

Preparation of Substituted 6-(Thienyloxy)pyrimidines

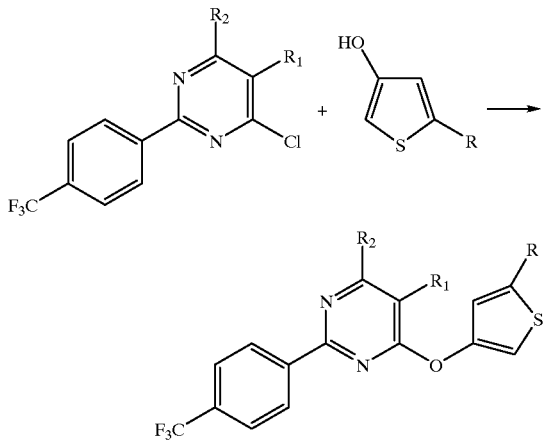

Using essentially the same procedure described in Example 14 and employing the appropriate 6-chloropyrimidine and 3-hydroxythiophene reactants the following compounds are obtained. All compounds shown on Table III are identified by $^1$HNMR, $^{13}$CNMR, $^{19}$FNMR, mass spectral and elemental analyses.

TABLE III

| Example Number | R | $R_1$ | $R_2$ | mp ° C. | % yield |
|---|---|---|---|---|---|
| 15 | $CH_3SO_2$ | H | $CH_3$ | 145–146 | 35 |
| 16 | $CF_3$ | $CH_3$ | H | 85–86 | 72 |
| 17 | $CH_3SO_2$ | $CH_3$ | H | 156–158 | 57 |
| 18 | $CF_3$ | H | $C_2H_5$ | 61–63 | 65 |
| 19 | $CF_3$ | H | $n-C_3H_7$ | 53–54.5 | 52 |
| 20 | $CF_3$ | $C_2H_5$ | Cl | 82.5–85 | 72 |
| 21 | $CF_3$ | H | Cl | 85–86 | 75 |
| 22 | $CF_3$ | H | $CH_2OCH_3$ | oil | 58 |
| 23 | $CO_2CH_3$ | H | $CH_3$ | 120–122 | 52 |
| 24 | $CH_2OH$ | H | $CH_3$ | 106–108 | 62 |
| 25 | CHO | H | $CH_3$ | 152–153.5 | 89 |
| 26 | $CO_2H$ | H | $CH_3$ | 203–204 | 86 |
| 27 | $CHF_2$ | H | $CH_3$ | 57–58 | 54 |

EXAMPLE 28

Preparation of 2-(α,α,α-Trifluoro-p-tolyl)-4,6-di{[5-(trifluoromethyl)-3-thienyl]oxy}pyrimidine

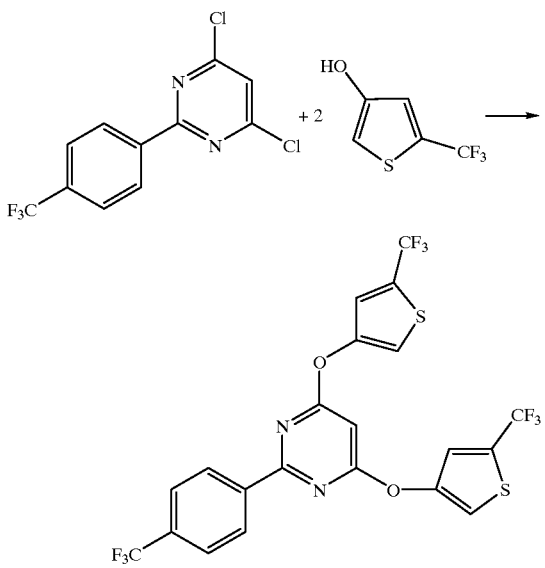

A mixture of 4,6-dichloro-2-(α,α,α-trifluoro-p-tolyl) pyrimidine (2.15 g, 7.34 mmol) and 3-hydroxy-2-(trifluoromethyl)thiophene (2.47 g, 14.7 mmol) in dimethylformamide is treated with $K_2CO_3$ (2.52 g, 18.3 mmol), heated at 100° C. for 3 hours, cooled to room temperature, poured onto water and neutralized with 6N HCL to pH 6–7. The resultant reaction mixture is extracted with ether. The ether extracts are washed sequentially with water and brine, dried over $MgSO_4$ and concentrated in vacuo to give a yellow solid residue. The residue is purified by flash chromatography (silica gel, methylene chloride) to afford the title product as an off-white solid, 3.03 g (74%), mp 93–95° C. identified by $^1$HNMR, $^{13}$CNMR, mass spectral and elemental analyses.

EXAMPLE 29

Preparation of 4-Methoxy-2-(α,α,α-trifluoro-p-tolyl)-6-{[5-(trifluoromethyl)-3-thienyl]oxy}pyrimidine

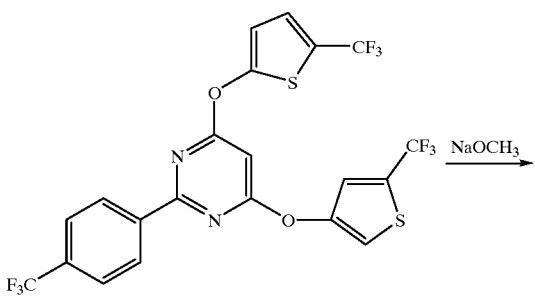

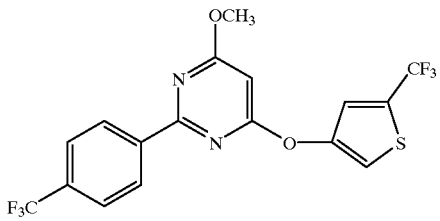

A solution of 2-(α,α,α-trifluoro-p-tolyl)-4,6-di{[5-(trifluoromethyl)-3-thienyl]oxy}pyrimidine (1.50 g, 2.70 mnol) in dimethylformamide is treated with 25% $NaOCH_3$ in methanol (0.58 g, 2.70 mmol), heated to 60° C. for 1.5 hours, cooled to room temperature, poured onto water and acidified to pH 5 with 6N HCl. The resultant reaction mixture is extracted with ether. The ether extracts are combined, washed sequentially with water and brine, dried over $MgSO_4$ and concentrated in vacuo to give a solid residue. The residue is chromatographed (silica gel, ethyl acetate/hexanes, 3/97) to afford the title product as a white solid, 0.58 g (51% yield), mp 91–93° C., identified by $^1$HNMR, $^{13}$CNMR, $^{19}$FNMR, mass spectral and elemental analyses.

EXAMPLE 30

Preparation of 5-Ethyl-2-(α,α,α-trifluoro-p-tolyl)-6-{[5-(trifluoromethyl)-3-thienyl]oxy}pyrimidine

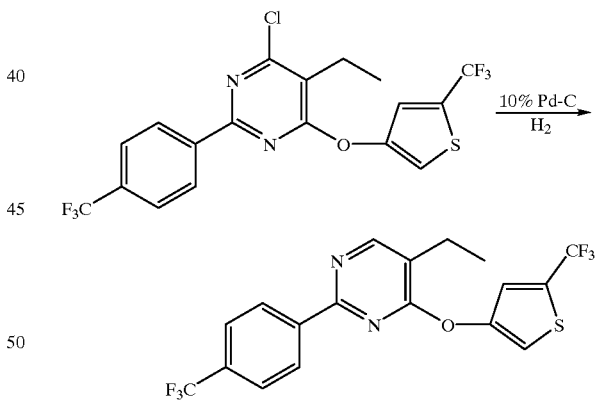

A solution of 4-Chloro-5-ethyl-2-(α,α,α-trifluoro-p-tolyl)-6-{[5-(trifluoromethyl)-3-thienyl]oxy}pyrimidine (1.06 g, 2.34 mmol) in a 1:1 mixture of methanol:ethyl acetate is treated with triethylamine (0.80 ml, 5.86 mmol) and 10% Pd-C (0.32 g, 30 wt %). The resultant mixture is placed on a PARR hydrogenator at 50 psi for 2 hours (reaction is complete by TLC). The resultant mixture is filtered. The filtrate is concentrated. The 20/80) to give the title product as a white solid, 0.69 9 (70%), mp 67–68° C. identified by $^1$HNMR, $^{13}$CNMR, $^{19}$FNMR, mass spectral and elemental analyses.

EXAMPLE 31

Preparation of 6-Bromo-4-methyl-2-{[5-(trifluoromethyl)-3-thienyl]oxy}pyridine

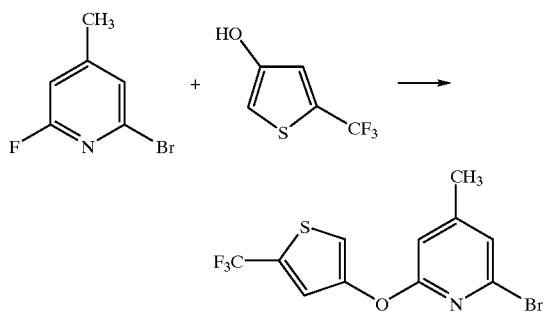

A solution of 2-bromo-6-fluoro-4-methyipyridine (1.00 g, 5.26 mmol) and 4-hydroxy-2-(trifluoromethyl)-thiophene (0.88 g, 5.26 mmol) in dimethylformamide is treated with K₂CO₃ (1.09 g, 7.89 mmol), heated at 80° C. for 23 hours, cooled to room temperature, poured onto water, acidified to pH 5–6 with 6N HCl and extracted with ether. The ether extracts are combined, washed sequentially with water and brine, dried over MgSQ₄ and concentrated in vacuo to give a residue. The residue is chromatographed (silica gel, ethyl acetate/hexanes, 3/97) to afford the title produce as a yellow oil, 1.16 g (65% yield), identified by ¹HNMR and ¹⁹FNMR analyses.

EXAMPLE 32

Preparation of 4-Methyl-6-(α,α,α-trifluoro-p-tolyl)-2-{[-(trifluoromethyl)-3-thienyl]oxy}pyridine

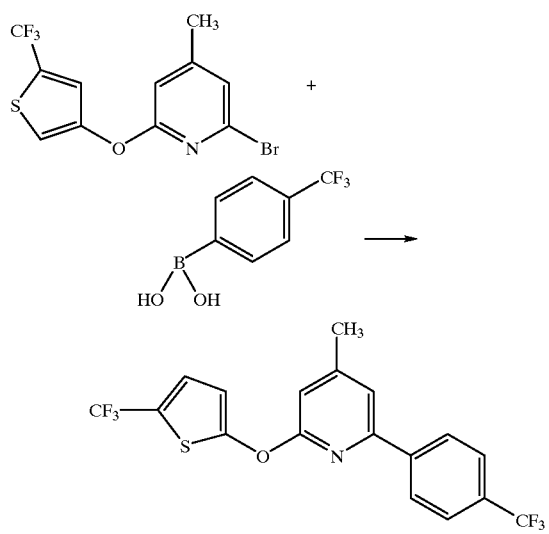

A solution of 6-bromo-4-methyl-2-{[5-(trifluoromethyl)-3-thienyl]oxy}pyridine (1.16 g, 3.43 mmol) in dimethoxy-ethane is treated with tetrakis(triphenylphosphine) Pd (79 mg, 0.069 mmol), stirred at room temperature for 30 minutes under N₂, treated with α,α,α-trifluoro-p-tolylboronic acid (0.72 g, 3.77 mmol), NaHCO₃ (0.95 g, 11.32 mmol) and water, heated at reflux temperature for 1.5 hours, cooled to room temperature, diluted with a mixture of ethyl acetate and water to give a two phase mixture. The phases are separated and the organic phase is set aside. The aqueous phase is extracted with ethyl acetate. The ethyl acetate extracts are combined with the organic phase, washed sequentially with water and brine, dried over MgSO₄ and concentrated in vacuo to give an amber oil residue. The residue is chromatographed (silica gel, ethyl acetate/hexanes, 5/95) to give the title product as a clear oil, which solidified upon drying in a Kugelrohr, to a waxy white solid, 1.22 g (88% yield), mp 52.5–55.5° C., identified by ¹HNMR, ¹³CNMR, ¹⁹FNMR, mass spectral and elemental analyses.

EXAMPLE 33 and 34

Preparation of Substituted 2-(Thienyloxy)pyridines

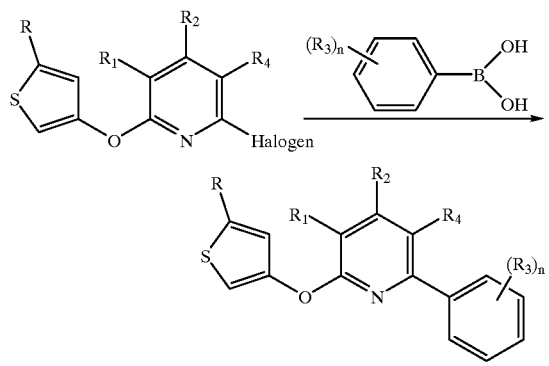

Using essentially the same procedures described in Examples 31 and 32 and employing the appropriately substuted 2,6-dihalopyridine substrate and phenylboronic acid, the compounds shown in Table IV are obtained.

TABLE IV

| Example Number | R | $R_1$ | $R_2$ | mp ° C. |
|---|---|---|---|---|
| 33 | $CF_3$ | H | CN | 86 |
| 34 | $CF_3$ | H | H | 61–63 |

EXAMPLE 35

Postemerqence Herbicidal Evaluation of Test Compounds

In this evaluation, test compounds are dispersed in an 80/20 acetone/water mixture containing 1% of a methylated crop oil. Concentrations of the test compound are sufficient to provide the equivalent of about 0.050 to 0.250 kg/ha of test compound when applied to the plants through a spray nozzle operating at 40 psi for a predetermined time. A variety of moncotyledonous and dicotyledonous plants are grown in potting soil, which is high in organic matter, until they are at the 2–3 leaf stage. The plants are sprayed with test solution, placed on greenhouse benches and cared for in a manner commensurate with conventional greenhouse practice. Approximately 3 weeks after treatment, visual ratings are made using the rating scale shown below. The data are shown on Table V.

PLANT SPECIES

| Bayer Code | Scientific Name | Common Name |
|---|---|---|
| ABUTH | *Abutilon theophrasti*, Medic. | Velvetleaf |
| AMBEL | *Ambrosia artemisiifolia*, L. | Ragweed |
| IPOHE | *Ipomoea hederacea*, (L) Jacq. | Morningglory |
| ECHCG | *Echinochloa crus-galli*, (L) Beau | Barnyardgrass |
| PANDI | *Panicum dichotomiflorum*, Michx | Panicum |
| GOSHI | *Gossypium hirsutum*, L. | Cotton |
| ZEAMX | *Zea mays* L. | Corn |

Rating Scale

| Rating | % Control (As Compared To Check) |
|---|---|
| 9 | 100 |
| 8 | 91–99 |
| 7 | 80–90 |
| 6 | 65–79 |
| 5 | 45–64 |
| 4 | 30–44 |
| 3 | 16–29 |
| 2 | 6–15 |
| 1 | 1–5 |
| 0 | No Effect |

EXAMPLE 36

Postemergence Herbicidal Evaluation of Test Compounds

In this evaluation, a variety of monocotyledonous and dicotyledonous plants are treated with a solution of the test compound in acetone containing 0.4% by weight of an alkylphenol/ethylene oxide condensate available under the trademark TRITON X-155 and diluted with water. The test solution is applied at dosage levels sufficient to supply about 0.025–0.400 kg/ha of test compound per treatment. Seedling plants which have been grown to the cotyledon to 2 leaf stage are sprayed with the test solution. After spraying, the plants are placed on greenhouse benches and cared for in the manner commensurate with conventional greenhouse practice. Approximately 21 days after treatment, the seedling plants are examined visually and rated on a 0–9 scale wherein a rating of 0 indicates no phytotoxic effect as compared to the untreated control and a rating of 9 indicates 100% control. An increase of 1 unit on a linear scale approximates a 12.4% increase in the level of effect. The data obtained are shown in Table VI. When more than one test is performed, the data are averaged.

PLANT SPECIES

| Bayer Code | Scientific Name | Common Name |
|---|---|---|
| ABUTH | *Abutilon theophrasti*, Medic. | Velvetleaf |
| AMBEL | *Ambrosia artemisiifolia*, L. | Ragweed |
| GALAP | *Galium aparine* | Galium |
| IPOHE | *Ipomoea hederacea*, (L) Jacq. | Morningglory |
| LAMPU | *Lamium purpureum*, L. | Red Deadnettle |
| MATIN | *Matricaria perforata* | Scentless Mayweed |
| DIGSA | *Digitaria sanguinalis*, (L) Scop | Crabgrass |
| ECHCG | *Echinochloa crus-galli*, (L) Beau | Barnyardgrass |
| SETVI | *Setaria viridis*, (L) Beau | Green Foxtail |
| ZEAMX | *Zea mays* L. | Corn |

TABLE V

Postemergence Herbicidal Evaluation of Test Compounds

| Example Number | Rate kg/ha | ABUTH | AMBEL | IPOHE | ECHCG | PANDI | GOSHI | ZEAMX |
|---|---|---|---|---|---|---|---|---|
| 14 | 0.2500 | 9.0 | 9.0 |  | 9.0 | 9.0 | 9.0 | 7.0 |
|  | 0.1250 | 8.0 | 8.0 |  | 9.0 | 9.0 | 8.0 | 6.0 |
|  | 0.0625 | 9.0 | 9.0 |  | 5.0 | 9.0 | 7.0 | 5.0 |
| 23 | 0.2000 | 4.0 | 4.0 | 2.0 | 3.0 | 2.0 | 3.0 | 3.5 |
|  | 0.1000 | 2.0 | 3.0 | 2.0 | 4.0 | 3.0 | 2.5 | 3.0 |
|  | 0.0500 | 3.0 | 2.0 | 1.0 | 3.0 | 3.0 | 1.5 | 3.5 |
| 24 | 0.2000 | 4.0 | 3.0 | 4.0 | 2.0 | 3.0 | 3.5 | 1.5 |
|  | 0.1000 | 3.0 | 2.0 | 4.0 | 5.0 | 4.0 | 3.5 | 1.0 |
|  | 0.0500 | 3.0 | 3.0 | 2.0 | 4.0 | 3.0 | 2.0 | 0.0 |
| 25 | 0.2000 | 3.0 | 3.0 | 4.0 | 3.0 | 2.0 | 4.0 | 2.0 |
|  | 0.1000 | 2.0 | 1.0 | 3.0 | 2.0 | 1.0 | 3.0 | 0.5 |
|  | 0.0500 | 4.0 | 1.0 | 3.0 | 2.0 | 1.0 | 3.0 | 1.0 |
| 26 | 0.2000 | 2.0 | 3.0 | 4.0 | 3.0 | 3.0 | 3.0 | 2.5 |
|  | 0.1000 | 2.0 | 2.0 | 3.0 | 3.0 | 3.0 | 2.0 | 2.0 |
|  | 0.0500 | 2.0 | 2.0 | 3.0 | 1.0 | 1.0 | 1.5 | 1.0 |
| 27 | 0.2000 | 7.0 | 7.0 | 7.0 | 6.0 | 5.0 | 7.5 | 5.0 |
|  | 0.1000 | 6.0 | 5.0 | 6.0 | 4.0 | 4.0 | 6.5 | 5.0 |
|  | 0.0500 | 4.0 | 5.0 | 5.0 | 3.0 | 5.0 | 5.0 | 4.0 |

TABLE VI

Postemergence Herbicidal Evaluation of Test Compounds

| Example Number | Rate kg/ha | ABUTH | AMBEL | GALAP | IPOHE | LAMPU | MATIN | DIGSA | ECHCG | SETVI | ZEAMX |
|---|---|---|---|---|---|---|---|---|---|---|---|
| 15 | 0.400 | 5.0 | | 4.0 | 8.0 | | 6.0 | | 4.0 | 6.0 | 3.0 |
|  | 0.100 | 4.0 | | 2.0 | 4.0 | | 3.0 | | 2.0 | 3.0 | 2.0 |
|  | 0.025 | 4.0 | | 2.0 | | | 3.0 | | 2.0 | 3.0 | 1.5 |
| 16 | 0.400 | 8.0 | 6.0 | 7.5 | 9.0 | 7.5 | 6.5 | 7.5 | 8.5 | 7.5 | 5.3 |
|  | 0.100 | 8.0 | 6.0 | 7.5 | 9.0 | 7.0 | 6.5 | 7.0 | 8.0 | 6.5 | 4.5 |
|  | 0.025 | 5.0 | | 7.0 | 9.0 | 6.0 | 5.0 | 7.0 | 6.0 | 7.0 | 4.0 |
| 17 | 0.400 | 5.0 | 4.0 | 6.0 | 9.0 | 8.0 | 8.0 | 3.0 | 5.0 | 7.0 | 2.5 |
|  | 0.100 | 3.0 | 3.0 | 3.0 | 5.0 | 5.0 | 7.0 | 1.0 | 3.0 | 4.0 | 1.5 |
|  | 0.025 | 2.0 | 3.0 | 1.0 | 4.0 | 3.0 | 5.0 | 1.0 | 1.0 | 3.0 | 1.0 |
| 18 | 0.400 | 7.0 | 6.0 | 7.0 | 9.0 | 7.0 | 7.0 | 8.0 | 8.0 | 6.0 | 4.5 |
|  | 0.100 | 7.0 | 6.0 | 7.0 | 9.0 | 7.0 | 5.0 | 6.0 | 8.0 | 6.0 | 3.5 |
|  | 0.025 | 6.0 | 2.0 | 7.0 | 9.0 | 7.0 | 5.0 | 5.0 | 6.0 | 4.0 | 3.0 |
| 19 | 0.400 | 6.0 | 5.0 | 7.0 | 9.0 | 7.0 | 7.0 | 7.0 | 7.0 | 7.0 | 4.0 |
|  | 0.100 | 6.0 | 4.0 | 7.0 | 9.0 | 7.0 | 5.0 | 5.0 | 5.0 | 5.0 | 2.5 |
|  | 0.025 | 3.0 | 2.0 | 5.0 | 7.0 | 5.0 | 3.0 | 4.0 | 2.0 | 4.0 | 2.0 |
| 20 | 0.400 | 0.0 | 4.0 | 2.0 | 3.0 | 3.0 | 3.0 | 0.0 | 0.0 | 0.0 | 0.5 |
|  | 0.100 | 0.0 | 3.0 | 1.0 | 1.0 | 2.0 | 2.0 | 0.0 | 0.0 | 0.0 | 0.5 |
|  | 0.025 | 0.0 | 3.0 | 1.0 | 0.0 | 1.0 | 1.0 | 0.0 | 0.0 | 0.0 | 0.0 |
| 21 | 0.400 | 5.0 | 7.0 | 8.0 | 9.0 | 8.0 | 8.0 | | | 8.0 | 4.0 |
|  | 0.100 | 4.0 | 7.0 | 7.0 | 9.0 | 8.0 | 8.0 | | | 8.0 | 3.0 |
|  | 0.025 | 3.0 | 7.0 | 7.0 | 9.0 | 7.0 | 7.0 | | | 6.0 | 2.5 |
| 29 | 0.400 | 7.0 | 6.0 | 7.0 | 9.0 | 7.0 | 7.0 | 7.0 | 8.0 | 6.0 | 5.0 |
|  | 0.100 | 6.0 | 6.0 | 7.0 | 9.0 | 7.0 | 7.0 | 6.0 | 7.0 | 6.0 | 3.5 |
|  | 0.025 | 5.0 | 5.0 | 6.0 | 9.0 | 7.0 | 6.0 | 5.0 | 7.0 | 5.0 | 3.5 |
| 30 | 0.400 | 7.0 | 6.0 | 8.0 | 9.0 | 7.0 | 7.0 | 7.0 | 8.0 | 7.0 | 5.0 |
|  | 0.100 | 7.0 | 6.0 | 7.0 | 9.0 | 7.0 | 6.0 | 6.0 | 8.0 | 6.0 | 4.0 |
|  | 0.025 | 4.0 | 5.0 | 6.0 | 9.0 | 7.0 | 5.0 | 5.0 | 7.0 | 5.0 | 3.0 |
| 32 | 0.400 | 7.0 | 5.0 | 7.0 | 9.0 | 7.0 | 6.0 | 7.0 | 8.0 | 6.0 | 5.0 |
|  | 0.100 | 6.0 | 5.0 | 7.0 | 9.0 | 7.0 | 6.0 | 6.0 | 8.0 | 5.0 | 4.0 |
|  | 0.025 | 6.0 | 3.0 | 7.0 | 9.0 | 7.0 | 5.0 | 5.0 | 7.0 | 4.0 | 3.5 |
| 33 | 0.400 | 8.0 | 7.0 | 7.0 | 9.0 | 8.0 | 8.0 | 7.0 | 7.0 | 8.0 | 3.0 |
|  | 0.100 | 5.0 | 6.0 | 7.0 | 9.0 | 8.0 | 8.0 | 4.0 | 4.0 | 7.0 | 3.0 |
|  | 0.025 | 2.0 | 4.0 | 6.0 | 6.0 | 8.0 | 7.0 | 2.0 | 2.0 | 4.0 | 1.0 |
| 34 | 0.400 | 9.0 | 8.0 | 8.0 | 9.0 | 8.0 | 8.0 | 8.0 | 9.0 | 8.0 | 6.0 |
|  | 0.100 | 9.0 | 7.0 | 8.0 | 9.0 | 8.0 | 8.0 | 8.0 | 8.0 | 8.0 | 5.0 |
|  | 0.025 | 7.0 | 5.0 | 8.0 | 9.0 | 8.0 | 8.0 | 4.0 | 4.0 | 8.0 | 3.0 |

EXAMPLE 37

Preemergence Herbicidal Evaluation of Test Compounds

In this evaluation, the seeds of a variety of monocotvledenous and dicotyledenous plants are individually mixed with sassafras sandy loam soil and placed on top of approximately one inch of said soil in separate cups. After planting, the cups are sprayed with an 80/20 acetone/water solution of test compound containing 1% methylated crop oil n sufficient quantity to provide about 0.0250–0.500 kg/ha of test compound per cup. The treated cups are placed on greenhouse benches and cared for in a manner commensurate with conventional greenhouse practice. Approximately 3 weeks after treatment, visual ratings are made using the rating system shown below. The data are shown on Table VII.

PLANT SPECIES

| Bayer Code | Scientific Name | Common Name |
|---|---|---|
| ABUTH | *Abutilon theophrasti*, Medic. | Velvetleaf |
| AMBEL | *Ambrosia artemisiifolia*, L. | Ragweed |
| IPOHE | *Ipomoea hederacea*, (L) Jacq. | Morningglory |
| ECHCG | *Echinochloa crus-galii*, (L) Beau | Barnyardgrass |
| PANDI | *Panicum dichotomiflorum*, Michx | Panicum |
| GOSHI | *Gossypium hirsutum*, L. | Cotton |
| ZEAMX | *Zea mays*, L. | Corn |

Rating Scale

| Rating | % Control (As Compared To Check) |
|---|---|
| 9 | 100 |
| 8 | 91–99 |
| 7 | 80–90 |
| 6 | 65–79 |
| 5 | 45–64 |
| 4 | 30–44 |
| 3 | 16–29 |
| 2 | 6–15 |
| 1 | 1–5 |
| 0 | No Effect |

TABLE VII

Preemergence Herbicidal Evaluation of Test Compounds

| Example Number | Rate kg/ha | ABUTH | AMBEL | IPOHE | ECHCG | PANDI | GOSHI | ZEAMX |
|---|---|---|---|---|---|---|---|---|
| 14 | 0.2500 | 9.0 | 9.0 |  | 9.0 | 9.0 | 9.0 | 5.0 |
|  | 0.1250 | 9.0 | 9.0 |  | 9.0 | 9.0 | 9.0 | 0.0 |
|  | 0.0625 | 9.0 | 7.0 |  | 7.0 | 8.0 | 5.0 | 1.0 |
| 23 | 0.2000 | 4.0 | 1.0 | 3.0 | 2.0 | 2.0 |  | 0.0 |
|  | 0.1000 | 0.0 | 1.0 | 3.0 | 2.0 | 2.0 |  | 0.0 |
|  | 0.0500 | 0.0 | 0.0 | 3.0 | 2.0 | 3.0 |  | 0.0 |
| 24 | 0.2000 | 1.0 | 3.0 | 0.0 | 1.0 | 3.0 |  | 0.0 |
|  | 0.1000 | 1.0 | 0.0 | 0.0 | 1.0 | 2.0 |  | 0.0 |
|  | 0.0500 | 0.0 | 0.0 | 2.0 | 1.0 | 2.0 |  | 0.0 |
| 25 | 0.2000 | 2.0 | 0.0 | 1.0 | 4.0 | 4.0 |  | 0.0 |
|  | 0.1000 | 1.0 | 0.0 | 0.0 | 3.0 | 3.0 |  | 0.0 |
|  | 0.0500 | 0.0 | 0.0 | 3.0 | 3.0 | 3.0 |  | 0.0 |
| 26 | 0.2000 | 0.0 | 1.0 | 1.0 | 2.0 | 2.0 |  | 0.0 |
|  | 0.1000 | 3.0 | 0.0 | 0.0 | 1.0 | 2.0 |  | 0.0 |
|  | 0.0500 | 4.0 | 0.0 | 0.0 | 2.0 | 1.0 |  | 0.0 |
| 27 | 0.2000 | 7.0 | 7.0 | 7.0 | 9.0 | 9.0 |  | 2.0 |
|  | 0.1000 | 4.0 | 4.0 | 6.0 | 5.0 | 6.0 |  | 1.0 |
|  | 0.0500 | 2.0 | 2.0 | 0.0 | 4.0 | 4.0 |  | 0.0 |

EXAMPLE 38

Preemergence Herbicidal Evaluation of Test Compounds

In this evaluation, seeds of a variety of monocotyledenous and dicotyledenous plants are sown on the soil surface and covered with a thin layer of soil. The soil used in this test is a prepared horticultural loam. One day after the seeds are sown, the soil is sprayed with a solution of the test compound in acetone containing 0.4% by weight of an alkylphenol ethylene oxide condensate available under the trademark TRITON X-155, which has been diluted with water. The test solution is applied at dosage levels corresponding to about 0.0125–0.400 kg/ha of test compound in a volume equivalent to 900 litres per hectare. After spraying, the pots are placed on greenhouse benches and cared for in a manner commensurate with conventional greenhouse practice. Approximately 21 days after treatment, the plants are evaluated visually and are rated on a 0–9 scale. A rating of 0 indicates no effect as compared to the untreated control and a rating of 9 indicates 100% control. An increase of 1 unit on the linear scale approximates a 12.4% increase in the level of effect. The data obtained are shown on Table VIII. When more than one test is performed, the data are averaged.

PLANT SPECIES

| Bayer Code | Scientific Name | Common Name |
|---|---|---|
| ABUTH | *Abutilon theophrasti*, Medic. | Velvetleaf |
| AMBEL | *Ambrosia artemisiifolia*, L. | Ragweed |
| GALAP | *Galium aparine* | Galium |
| IPOHE | *Ipomomea hederacea*, (L) Jacq. | Morningglory |
| LAMPU | *Lamium purpureum*, L. | Red Deadnettle |
| MATIN | *Matricaria perforata* | Scentless Mayweed |
| DIGSA | *Digitaria sanguinalis*, (L) Scop | Crabgrass |
| ECHCG | *Echinochloa crus-galli*, (L) Beau | Barnyardgrass |
| SETVI | *Setaria viridis*, (L) Beauv | Green Foxtail |
| ZEAMX | *Zea mays*, L. | Corn |

TABLE VIII

Preemergence Herbicidal Evaluation of Test Compounds

| Example Number | Rate kg/ha | ABUTH | AMBEL | IPOHE | MATIN | DIGSA | ECHCG | SETVI | ZEAMX |
|---|---|---|---|---|---|---|---|---|---|
| 15 | 0.4000 | 8.0 |  | 7.0 | 9.0 |  | 4.0 | 9.0 | 1.5 |
|  | 0.1000 | 5.0 |  | 3.0 | 9.0 |  | 3.0 | 5.0 | 1.5 |
|  | 0.0250 | 4.0 |  | 3.0 | 8.0 |  | 1.0 | 2.0 | 1.0 |
|  | 0.0125 | 4.0 |  |  | 8.0 |  | 0.0 | 1.0 | 0.5 |
| 16 | 0.4000 | 9.0 |  | 9.0 | 9.0 | 9.0 | 9.0 | 9.0 | 5.0 |
|  | 0.1000 | 9.0 |  | 9.0 | 9.0 | 8.0 | 7.0 | 9.0 | 4.0 |
|  | 0.0250 | 9.0 |  | 9.0 | 8.0 |  | 6.0 | 8.0 | 3.0 |
|  | 0.0125 | 8.0 |  | 9.0 | 9.0 | 8.0 | 9.0 | 9.0 | 2.0 |
| 17 | 0.4000 | 4.0 | 6.0 | 2.0 | 8.0 |  | 4.0 | 6.0 | 0.5 |
|  | 0.1000 | 2.0 | 6.0 | 1.0 | 8.0 |  | 2.0 | 3.0 | 0.5 |
|  | 0.0250 | 1.0 | 3.0 | 1.0 | 4.0 |  | 1.0 | 2.0 | 0.0 |

TABLE VIII-continued

Preemergence Herbicidal Evaluation of Test Compounds

| Example Number | Rate kg/ha | ABUTH | AMBEL | IPOHE | MATIN | DIGSA | ECHCG | SETVI | ZEAMX |
|---|---|---|---|---|---|---|---|---|---|
| 18 | 0.4000 | 9.0 | | 9.0 | 8.0 | | 9.0 | 9.0 | 4.0 |
| | 0.1000 | 4.0 | | 6.0 | 8.0 | | 7.0 | 9.0 | 3.0 |
| | 0.0250 | 4.0 | | 6.0 | 8.0 | | 6.0 | 9.0 | 2.0 |
| | 0.0125 | 3.0 | | 2.0 | 6.0 | | 4.0 | 9.0 | 1.0 |
| 19 | 0.4000 | 5.0 | | 7.0 | 8.0 | | 7.0 | 9.0 | 2.5 |
| | 0.1000 | 3.0 | | 3.0 | 8.0 | | 5.0 | 9.0 | 1.0 |
| | 0.0250 | 2.0 | | 2.0 | 5.0 | | 2.0 | 6.0 | 1.0 |
| | 0.0125 | 1.0 | | 2.0 | 4.0 | | 1.0 | 3.0 | 0.5 |
| 20 | 0.4000 | 0.0 | 4.0 | 0.0 | 3.0 | | 0.0 | 0.0 | 0.0 |
| | 0.1000 | 0.0 | | 0.0 | 1.0 | | 0.0 | 0.0 | 0.0 |
| 21 | 0.4000 | 4.0 | | 8.0 | 8.0 | | 8.0 | 9.0 | 4.0 |
| | 0.1000 | 3.0 | | 7.0 | 8.0 | | 7.0 | 9.0 | 3.0 |
| | 0.0250 | 2.0 | | 3.0 | 8.0 | | 5.0 | 9.0 | 2.0 |
| | 0.0125 | 2.0 | | 2.0 | 6.0 | | 4.0 | 7.0 | 1.0 |
| 29 | 0.4000 | 9.0 | | 9.0 | 9.0 | | 8.0 | 9.0 | 4.0 |
| | 0.1000 | 7.0 | | 5.0 | 8.0 | | 7.0 | 9.0 | 3.0 |
| | 0.0250 | 6.0 | | 4.0 | 8.0 | | 6.0 | 9.0 | 2.0 |
| | 0.0125 | 3.0 | | 2.0 | 7.0 | | 3.0 | 9.0 | 1.0 |
| 30 | 0.4000 | 9.0 | 9.0 | 9.0 | 8.0 | | 9.0 | 9.0 | 4.0 |
| | 0.1000 | 6.0 | 8.0 | 3.0 | 8.0 | | 8.0 | 9.0 | 2.5 |
| | 0.0250 | 5.0 | 7.0 | 3.0 | 8.0 | | 6.0 | 9.0 | 2.0 |
| | 0.0125 | 2.0 | 5.0 | 2.0 | 7.0 | | 3.0 | 8.0 | 1.0 |
| 33 | 0.4000 | 8.0 | 9.0 | 3.0 | 9.0 | 8.0 | 5.0 | 9.0 | 2.0 |
| | 0.1000 | 3.0 | 7.0 | 1.0 | 9.0 | 4.0 | 1.0 | 5.0 | 1.0 |
| | 0.0250 | 0.0 | 3.0 | 1.0 | 6.0 | 1.0 | 0.0 | 1.0 | 1.0 |
| 34 | 0.4000 | 9.0 | 8.0 | 9.0 | 9.0 | 9.0 | 9.0 | 9.0 | 4.0 |
| | 0.1000 | 9.0 | 8.0 | 9.0 | 9.0 | 9.0 | 8.0 | 9.0 | 3.0 |
| | 0.0250 | 5.0 | 8.0 | 2.0 | 8.0 | 8.0 | 4.0 | 9.0 | 2.0 |
| | 0.0125 | 4.0 | 7.0 | | 8.0 | 5.0 | 2.0 | 8.0 | 2.0 |

What is claimed is:
1. A compound having the structure of formula I

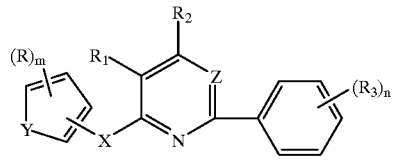

(I)

wherein X and Y are each independently O or S;
Z s N;
m is 0 or an integer of 1, 2 or 3;
n is 0 or an integer of 1, 2, 3, 4 or 5;
R is halogen, $C_1$–$C_6$alkyl optionally substituted with one or more halogen, $C_1$–$C_4$alkoxy, $C_1$–$C_4$haloalkoxy, $C_1$–$C_4$alkoxycarbonyl, OH, CN, $NO_2$, $R_5SO_z$, CY'$R_7$, or phenyl groups,
$C_2$–$C_6$alkenyl optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_5SO_z$, or phenyl groups,
$C_3$–$C_6$alkynyl optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_5SO_z$, or phenyl groups,
$C_1$–$C_6$alkoxy optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_5SO_z$, or phenyl groups,
phenyl optionally substituted with one or more halogen, $C_1$–$C_4$alkyl, $C_1$–$C_4$haloalkyl, $C_1$–$C_4$alkoxy, $C_1$–$C_4$haloalkoxy, $R_5SO_z$, CN, $NO_2$, $CO_2R_6$ or CY'$R_7$ groups,
$R_5SO_z$, $NO_2$, CN, $CO_2R_6$, CY'$R_7$, $OR_8$, $OCOR_9$ or $NR_{10}R_{11}$;
$R_1$ and $R_2$ are each independently H, halogen, $C_1$–$C_6$alkyl optionally substituted with one or more halogen, $C_1$–$C_4$alkoxy, $C_1$–$C_4$alkylthio, $C_1$–$C_4$haloalkoxy, $C_1$–$C_4$alkoxycarbonyl, OH, CHO, CN, $NO_2$, $R_{11}SO_x$, or phenyl groups,
$C_2$–$C_6$alkenyl optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_{11}SO_x$, or phenyl groups,
$C_3$–$C_6$alkynyl optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_{11}SO_x$, or phenyl groups,
$C_1$–$C_6$alkoxy optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_{11}SO_x$, or phenyl groups,
$R_{11}SO_x$, $NR_{12}R_{13}$, CN, CZ'$R_{14}$ or formamidine radical;
$R_3$ is halogen, $C_1$–$C_6$alkyl optionally substituted with one or more halogen, $C_1$–$C_4$alkoxy, $C_1$–$C_4$haloalkoxy, $C_1$–$C_4$alkoxycarbonyl, OH, CX'$R_{15}$, CN, $NO_2$, $R_{16}SO_y$, or phenyl groups,
$C_2$–$C_6$alkenyl optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_{16}SO_y$, or phenyl groups,
$C_3$–$C_6$alkynyl optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_{16}SO_y$, or phenyl groups,
$C_1$–$C_6$alkoxy optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_{16}SO_y$, or phenyl groups, $R_{16}SO_y$, $NR_{17}R_{18}$, $NO_2$, CN, $CX'R_{15}$, $CO_2R_{19}$ or $OCOR_{20}$;

X', Y' and Z' are each independently O, $NOR_{21}$ or $NNR_{22}R_{23}$;

$R_5$, $R_{11}$, and $R_{16}$ are each independently $C_1$–$C_4$alkyl or $C_1$–$C_4$haloalkyl;

$R_6$, $R_7$, $R_9$, $R_{14}$, $R_{15}$, $R_{19}$ and $R_{20}$ are each independently H or $C_1$–$C_4$alkyl optionally substituted with one or more halogen, phenyl or furyl groups;

$R_8$ is H, $C_1$–$C_6$alkyl optionally substituted with one or more halogen, $C_1$–$C_4$alkoxy, $C_1$–$C_4$haloalkoxy, $C_1$–$C_4$alkoxycarbonyl, OH, CN, or $NO_2$ groups, phenyl optionally substituted with one or more halogen, $C_1$–$C_4$alkoxy, $C_1$–$C_4$haloalkoxy, $C_1$–$C_4$alkoxycarbonyl, OH, CN or $NO_2$ groups;

$R_{10}$, $R_{11}$, $R_{12}$, $R_{13}$, $R_{17}$, $R_{18}$, $R_{22}$ and $R_{23}$ are each independently H, $C_1$–$C_4$alkyl or $C_1$–$C_4$alkoxy;

$R_{21}$ is H or $C_1$–$C_4$alkyl; and x, y and z are each independently 0 or an integer of 1 or 2.

2. The compound according to claim 1 wherein X is O.

3. The compound according to claim 1 wherein Y is S.

4. The compound according to claim 1 having the structure of formula IA

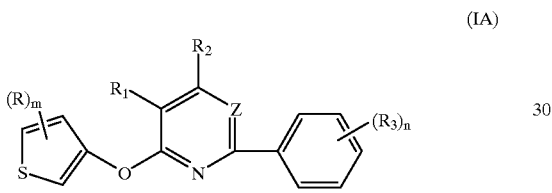

(IA)

wherein Z, R, $R_1$, $R_2$, $R_3$, m and n are as defined in claim 1.

5. The compound according to claim 4 wherein n is 0 or an integer of 1, 2 or 3;

R is halogen, $R_5SO_2$, $CO_2R_6$, $COR_7$, CN, CHO, $NO_2$, $C_1$–$C_6$alkyl or $C_1$–$C_6$haloalkyl;

$R_1$ and $R_2$ are each independently H, halogen, $C_1$–$C_6$alkyl optionally substituted with one or more halogen, $C_1$–$C_4$alkoxy, $C_1$–$C_4$haloalkoxy or $C_1$–$C_4$alkylthio groups; $C_1$–$C_6$alkoxy, $R_{10}SO_x$ or CN;

$R_3$ is halogen, $C_1$–$C_6$alkyl, $C_1$–$C_6$haloalkyl or $R_{16}SO_y$;

$R_5$, $R_{10}$ and $R_{16}$ are each independently $C_1$–$C_4$alkyl or $C_1$–$C_6$haloalkyl;

$R_6$ and $R_7$ are each independently $C_1$–$C_6$alkyl or $C_1$–$C_6$haloalkyl;

y and z are each independently 0 or an integer of 1 or 2; and x is 0.

6. The compound according to claim 5 wherein m is 1; R is attached to the 5-position of the thienyloxy group; n is 1; and $R_3$ is attached to the 4-position of the phenyl group.

7. The compound according to claim 6 wherein R is $C_1$–$C_4$haloalkyl, $C_1$–$C_4$haloalkylcarbonyl, $C_1$–$C_4$alkylsulfonyl or $C_1$–$C_4$haloalkylsulfonyl; $R_1$ and $R_2$ are each independently H, halogen, $C_1$–$C_4$alkoxy or $C_1$–$C_4$alkyl optionally substituted with one or more $C_1$–$C_4$alkoxy groups; and $R_3$ is $CF_3$.

8. The compound according to claim 6 wherein $R_1$ and $R_2$ are each independently H, halogen, $C_1$–$C_4$alkoxy or $C_1$–$C_4$alkyl optionally substituted with one or more $C_1$–$C_4$alkoxy groups.

9. The compound according to claim 8 wherein R and $R_3$ are each $CF_3$; and $R_1$ and $R_2$ are each independently H, halogen, $C_1$–$C_4$alkoxy or $C_1$–$C_4$alkyl optionally substituted with one or more $C_1$–$C_4$alkoxy groups.

10. A compound according to claim 8 selected from the group consisting of 4-Methyl-2-($\alpha,\alpha,\alpha$-trifluoro-p-tolyl)-6-{[5-(trifluoromethyl)-3-thienyl]oxy}-pyrimidine;

4-Methoxy-2-($\alpha,\alpha,\alpha$-trifluoro-p-tolyl)-6-{[5-(trifluoromethyl-3-thienyl]oxy}pyrimidine;

5-Ethyl-2-($\alpha,\alpha,\alpha$-trifluoro-p-tolyl)-6-{[5-(trifluoromethyl-3-thienyl]oxy}pyrimidine;

4-Methyl-6-($\alpha,\alpha,\alpha$-trifluoro-p-tolyl)-2-{[5-(trifluoromethyl)-3-thienyl]oxy}pyrimidine;

5-Methyl-2-($\alpha,\alpha,\alpha$-trifluoro-p-tolyl)-6-{[5-(trifluoromethyl-3-thienyl]oxy}pyrimidine;

5-Ethyl-2-($\alpha,\alpha,\alpha$-trifluoro-p-tolyl)-6-{[5-(trifluoromethylsulfonyl)3-thienyl]oxy}pyrimidine;

4-Ethyl-2-($\alpha,\alpha,\alpha$-trifluoro-p-tolyl)-6-{[5-(trifluoromethyl-3-thienyl]oxy}pyrimidine;

2-($\alpha,\alpha,\alpha$-Trifluoro-p-tolyl)-6-{[5-(trifluoromethyl-3-thienyl]oxy}pyrimidine;

4-n-Propyl-2-($\alpha,\alpha,\alpha$-trifluoro-p-tolyl)-6-{[5-(trifluoromethyl-3-thienyl]oxy}pyrimidine;

4-Chloro-5-ethyl-2-($\alpha,\alpha,\alpha$-trifluoro-p-tolyl)-6-{[5-(trifluoromethyl-3-thienyl]oxy}pyrimidine;

4-Chloro-2-($\alpha,\alpha,\alpha$-trifluoro-p-tolyl)-6-{[5-(trifluoromethyl-3-thienyl]oxy}pyrimidine;

4-(Methoxymethyl)-2-($\alpha,\alpha,\alpha$-trifluoro-p-tolyl)-6-{[5-(trifluoromethyl-3-thienyl]oxy}pyrimidine;

4-Methyl-2-($\alpha,\alpha,\alpha$-trifluoro-p-tolyl)-6-{[5-(hydroxymethyl)-3-thienyl]oxy}pyrimidine;

4-(Difluoromethyl)-2-($\alpha,\alpha,\alpha$-trifluoro-p-tolyl)-6-{[5-(trifluoromethyl-3-thienyl]oxy}pyrimidine;

5-Ethyl-2-($\alpha,\alpha,\alpha$-trifluoro-p-tolyl)-6-{[5-(trifluoromethylsulfonyl)-3-thienyl]oxy}pyrimidine;

5-Methyl-2-($\alpha,\alpha,\alpha$-trifluoro-p-tolyl)-6-{[5-(methylsulfonyl)-3-thienyl]oxy}pyrimidine;

4-Methoxy-2-($\alpha,\alpha,\alpha$-trifluoro-p-tolyl)-6-[(5-formyl-3-thienyl)oxy]pyrimidine;

4-Ethyl-2-($\alpha,\alpha,\alpha$-trifluoro-p-tolyl)-6-{[5-(methylsulfonyl)-3-thienyl]oxy}pyrimidine;

4-Methyl-2-($\alpha,\alpha,\alpha$-trifluoro-p-tolyl)-6-{[5-(trifluoromethylsulfonyl)-3-thienyl]oxy}pyrimidine;

4-Cyano-2-($\alpha,\alpha,\alpha$-trifluoro-p-tolyl)-6-{[5-(methylsulfonyl)-3-thienyl]oxy}pyrimidine; and 5-1Methoxymethyl-2-($\alpha,\alpha,\alpha$-trifluoro-p-tolyl)-6-{[5-(trifluoromethylsulfonyl)-3-thienyl]oxy}pyrimidine.

11. A method for the control of monocotyledenous and dicotyledenous annual, perennial and aquatic plant species which comprises applying to the foliage of said plants or to the soil or water containing the seeds or other propagating organs thereof a herbicidally effective amount of a compound having the structure of formula I

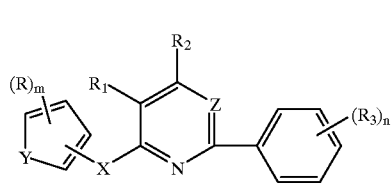

(I)

wherein X, Y, Z, m, n, R, $R_1$, $R_2$ and $R_3$ are as defined in claim 1.

12. The method according to claim 11 having

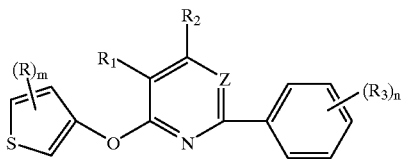

13. The method according to claim 12 wherein m and n are each 1; R is attached to the 5 position of the thienyloxy group; and $R_3$ is attached to the 4 position of the phenyl group.

14. The method according to claim 11 wherein the compound is applied at a rate of about 0.001 kg/ha to 10.0 kg/ha.

15. A herbicidal compositon which comprises an inert solid or liquid carrier and a herbicidally effective amount of a compound having the structure of formula I

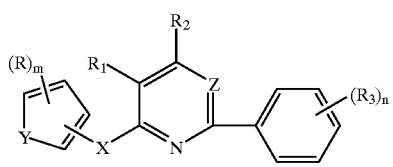

(I)

wherein X, Y, Z, m, n, $R_1$, $R_2$ and $R_3$ are as defined in claim 1.

16. The composition according to claim 15 having the structure of formula

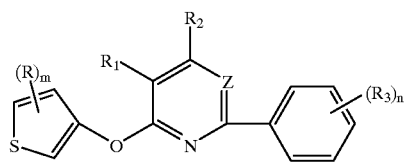

17. The composition according to claim 16 wherein m and n are each 1; R is attached to the 5 position of the thienyloxy group; and $R_3$ is attached to the 4 position of the phenyl group.

18. A process for the preparation of a compound having the structure of formula I

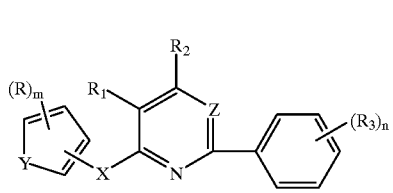

(I)

wherein X and Y are each independently O or S;
Z is N;
m is 0 or an integer of 1, 2 or 3;
n is 0 or an integer of 1, 2, 3, 4 or 5;
R is halogen, $C_1$–$C_6$alkyl optionally substituted with one or more halogen, $C_1$–$C_4$alkoxy, $C_1$–$C_4$haloalkoxy, $C_1$–$C_4$alkoxycarbonyl, OH, CN, $NO_2$, $R_5SO_z$, CY'$R_7$, or phenyl groups,
  $C_2$–$C_6$alkenyl optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_5SO_z$, or phenyl groups,
  $C_3$–$C_6$alkynyl optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_5SO_z$, or phenyl groups,
  $C_1$–$C_6$alkoxy optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_5SO_z$, or phenyl groups,
  phenyl optionally substituted with one or more halogen, $C_1$–$C_4$alkyl, $C_1$–$C_4$haloalkyl, $C_1$–$C_4$alkoxy, $C_1$–$C_4$haloalkoxy, $R_5SO_z$, CN, $NO_2$, $CO_2R_6$ or CY'$R_7$ groups,
  $R_5SO_z$, $NO_2$, CN, $CO_2R_6$, CY'$R_7$, $OR_8$, $OCOR_9$ or $NR_{10}R_{11}$;
$R_1$ and $R_2$ are each independently H, halogen, $C_1$–$C_6$alkyl optionally substituted with one or more halogen, $C_1$–$O_4$alkoxy, $C_1$–$C_4$haloalkoxy, $C_1$–$C_4$haloalkoxy, $C_1$–$C_4$alkoxycarbonyl, OH, CHO, CN, $NO_2$, $R_{11}SO_x$, or phenyl groups,
  $C_2$–$C_6$alkenyl optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_{11}SO_x$, or phenyl groups,
  $C_3$–$C_6$alkynyl optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_{11}SO_x$, or phenyl groups,
  $C_1$–$C_6$alkoxy optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_{11}SO_x$, or phenyl groups,
  $R_{11}SO_x$, $NR_{12}R_{13}$, CN, CZ'$R_{14}$ or formamidine radical;
$R_3$ is halogen, $C_1$–$C_6$alkyl optionally substituted with one or more halogen, $C_1$–$C_4$alkoxy, $C_1$–$C_4$haloalkoxy, $C_1$–$C_4$alkoxycarbonyl, OH, CX'$R_{15}$, CN, $NO_2$, $R_{16}SO_y$ or phenyl groups,
  $C_2$–$C_6$alkenyl optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_{16}SO_y$ or phenyl groups,
  $C_3$–$C_6$alkynyl optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_{16}SO_y$ or phenyl groups,
  $C_1$–$C_6$alkoxy optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_{16}SO_y$ or phenyl groups,
  $R_{16}SO_y$, $NR_{17}R_{18}$, $NO_2$, CN, CX'$R_{15}$, $CO_2R_{19}$ or $OCOR_{20}$;
X', Y' and Z' are each independently O, $NOR_{21}$ or $NNR_{22}R_{23}$;
$R_5$, $R_{11}$, and $R_{16}$ are each independently $C_1$–$C_4$alkyl or $C_1$–$C_4$haloalkyl;
$R_6$, $R_7$, $R_9$, $R_{14}$, $R_{15}$, $R_{19}$ and $R_{20}$ are each independently H or $C_1$–$C_4$alkyl optionally substituted with one or more halogen, phenyl or furyl groups;
$R_8$ is H, $C_1$–$C_6$alkyl optionally substituted with one or more halogen, $C_1$–$C_4$alkoxy, $C_1$–$C_4$haloalkoxy, $C_1$–$C_4$alkoxycarbonyl, OH, CN, or $NO_2$ groups,
  phenyl optionally substituted with one or more halogen, $C_1$–$C_4$alkoxy, $C_1$–$C_4$haloalkoxy, $C_1$–$C_4$alkoxycarbonyl, OH, CN or $NO_2$ groups;
$R_{10}$, $R_{11}$, $R_{12}R_{13}$, $R_{17}$, $R_{18}$, $R_{22}$ and $R_{23}$ are each independently H, $C_1$–$C_4$alkyl or $C_1$–$C_4$alkoxy;

$R_{21}$ is H or $C_1$–$C_4$alkyl; and x, y and z are each independently 0 or an integer of 1 or 2 which comprises reacting a compound of formula II

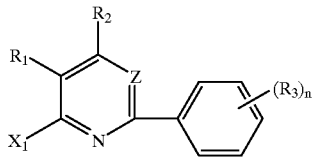 (II)

wherein $X_1$ is Cl, Br or F and Z, $R_1$, $R_2$, $R_3$ and n are as defined hereinabove for formula I with at least one molar equivalent of a compound of formula III

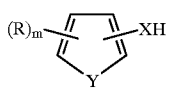 (III)

wherein R, m and X is defined hereinabove for formula I in the presence of a base and a solvent.

19. A compound having the structure of formula IV

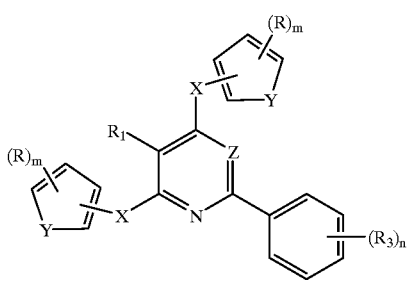 (IV)

wherein X and Y are each independently O or S;

Z is N;

m is 0 or an integer of 1, 2 or 3;

n is 0 or an integer of 1, 2, 3, 4 or 5;

R is halogen, $C_1$–$C_6$alkyl optionally substituted with one or more halogen, $C_1$–$C_4$alkoxy, $C_1$–$C_4$haloalkoxy, $C_1$–$C_4$alkoxycarbonyl, OH, CN, $NO_2$, $R_5SO_z$, $CY'R_7$, or phenyl groups, $C_2$–$C_6$alkenyl optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_5SO_z$, or phenyl groups, $C_3$–$C_6$alkynyl optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_5SO_z$, or phenyl groups, $C_1$–$C_6$alkoxy optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_5SO_z$, or phenyl groups, phenyl optionally substituted with one or more halogen, $C_1$–$C_4$alkyl, $C_1$–$C_4$haloalkyl, $C_1$–$C_4$alkoxy, $C_1$–$C_4$haloalkoxy, $R_5SO_z$, CN, $NO_2$, $CO_2R_6$ or $CY'R_7$ groups, $R_5SO_z$, $NO_2$, CN, $CO_2R_6$, $CY'R_7$, $OR_8$, $OCOR_9$ or $NR_{10}R_{11}$;

$R_1$ is H, halogen, $C_1$–$C_6$alkyl optionally substituted with one or more halogen, $C_1$–$C_4$alkoxy, $C_1$–$C_4$alkylthio, $C_1$–$C_4$haloalkoxy, $C_1$–$C_4$alkoxycarbonyl, OH, CHO, CN, $NO_2$, $R_{11}SO_x$, or phenyl groups, $C_2$–$C_6$alkenyl optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_{11}SO_x$, or phenyl groups, $C_3$–$C_6$alkynyl optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_{11}SO_x$, or phenyl groups, $C_1$–$C_6$alkoxy optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_{11}SO_x$, or phenyl groups, $R_{11}SO_x$, $NR_{12}R_{13}$, CN, $CZ'R_{14}$ or formamidine radical;

$R_3$ is H, halogen, $C_1$–$C_6$alkyl optionally substituted with one or more halogen, $C_1$–$C_4$alkoxy, $C_1$–$C_4$haloalkoxy, $C_1$–$C_4$alkoxycarbonyl, OH, $CX'R_{15}$, CN, $NO_2$, $R_{16}SO_y$ or phenyl groups, $C_2$–$C_6$alkenyl optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_{16}SO_y$ or phenyl groups, $C_3$–$C_6$alkynyl optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_{16}SO_y$ or phenyl groups, $C_1$–$C_6$alkoxy optionally substituted with one or more halogen, $C_1$–$C_4$alkoxy, $C_1$–$C_4$haloalkoxy, $C_1$–$C_4$alkoxycarbonyl, OH, CHO, CN, $NO_2$, $R_{16}SO_y$ or phenyl groups, $R_{16}SO_y$, $NR_{17}R_{18}$, $NO_2$, CN, $CX'R_{15}$, $CO_2R_{19}$ or $OCOR_{20}$;

X', Y' and Z' are each independently O, $NOR_{21}$ or $NNR_{22}R_{23}$;

$R_5$, $R_{11}$, and $R_{16}$ are each independently $C_1$–$C_4$alkyl or $C_1$–$C_4$haloalkyl;

$R_6$, $R_7$, $R_9$, $R_{14}$, $R_{15}$, $R_{19}$ and $R_{20}$ are each independently H or $C_1$–$C_4$alkyl optionally substituted with one or more halogen, phenyl or furyl groups;

$R_8$ is H, $C_1$–$C_6$alkyl optionally substituted with one or more halogen, $C_1$–$C_4$alkoxy, $C_1$–$C_4$haloalkoxy, $C_1$–$C_4$alkoxycarbonyl, OH, CN, or $NO_2$ groups, phenyl optionally substituted with one or more halogen, $C_1$–$C_4$alkoxy, $C_1$–$C_4$haloalkoxy, $C_1$–$C_4$alkoxycarbonyl, OH, CN or $NO_2$ groups;

$R_{10}$, $R_{11}$, $R_{12}$, $R_{13}$, $R_{17}$, $R_{18}$, $R_{22}$ and $R_{23}$ are each independently H, $C_1$–$C_4$alkyl or $C_1$–$C_4$alkoxy;

$R_{21}$ is H or $C_1$–$C_4$alkyl; and x, y and z are each independently 0 or an integer of 1 or 2.

20. The compound according to claim 19 having the structure of formula IVA

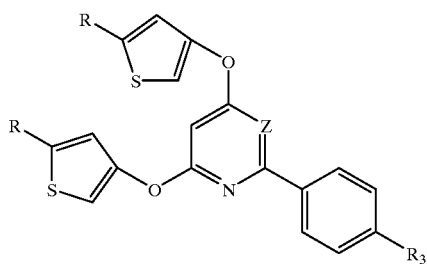
(IVA)
wherein Z, R and R₃ are as defined in claim 19.
21. The compound according to claim 20 wherein R is $CF_3$ or $SO_2CH_3$ and $R_3$ is $CF_3$.
* * * * *